US012649765B2

(12) United States Patent
Polt et al.

(10) Patent No.: US 12,649,765 B2
(45) Date of Patent: Jun. 9, 2026

(54) OXYTOCIN ANALOGUES AND METHODS FOR USING THE SAME

(71) Applicant: Arizona Board of Regents on Behalf of the University of Arizona, Tucson, AZ (US)

(72) Inventors: Robin L. Polt, Tucson, AZ (US); Lajos Z. Szabo, Tucson, AZ (US); John M. Streicher, Tucson, AZ (US); Parthasaradhireddy Tanguturi, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 594 days.

(21) Appl. No.: 18/006,841

(22) PCT Filed: Jul. 27, 2021

(86) PCT No.: PCT/US2021/043305
§ 371 (c)(1),
(2) Date: Jan. 25, 2023

(87) PCT Pub. No.: WO2022/026463
PCT Pub. Date: Feb. 3, 2022

(65) Prior Publication Data

US 2023/0265124 A1 Aug. 24, 2023

Related U.S. Application Data

(60) Provisional application No. 63/056,930, filed on Jul. 27, 2020.

(51) Int. Cl.

| | |
|---|---|
| ***C07K 7/16*** | (2006.01) |
| ***A61P 29/00*** | (2006.01) |
| *A61K 38/00* | (2006.01) |

(52) U.S. Cl.
CPC ................ *C07K 7/16* (2013.01); *A61P 29/00* (2018.01); *A61K 38/00* (2013.01)

(58) Field of Classification Search
CPC . C07K 7/16; A61P 29/00; A61P 25/04; A61K 38/00
See application file for complete search history.

(56) References Cited

U.S. PATENT DOCUMENTS

| | | | |
|---|---|---|---|
| 5,026,703 | A | 6/1991 | Bock et al. |
| 5,990,273 | A | 11/1999 | Andersson et al. |
| 2011/0044905 | A1 | 2/2011 | Alagarsamy et al. |

OTHER PUBLICATIONS

Smith (Journal of Medicinal Chemistry, 1978, 21(1), 117-20) (Year: 1978).*
Rodriguez (Peptide Modifications to Increase Metabolic Stability and Activity, Methods in Molecular Biology, 2013, vol. 1081, Chapter 8; Predrag Cudic (ed.) (Year: 2013).*
Sola (Biodrugs, 2010, 24(1), 9-21), Seitz (Chembiochem, 2000, 1, 214-246) (Year: 2000).*
Yamasue (Curr Topics Behav Neurosci., 2018, 35, 449-466). (Year: 2018).*
Seitz (Chembiochem, 2000, 1, 214-246) (Year: 2000).*
International Search Report issued in corresponding International Patent Application No. PCT/US2021/043305.

* cited by examiner

*Primary Examiner* — Sudhakar Katakam
(74) *Attorney, Agent, or Firm* — Cozen O'Connor

(57) ABSTRACT

The present invention provides cyclic oligopeptides and methods for using the same. The cyclic oligopeptides of the invention are analogues of oxytocin wherein the disulfide linkage between $Cys^1$ and $Cys^2$ are replaced with a more stable amide bond. The cyclic oligopeptides of the invention can also include a glycoside to increase blood-brain barrier penetration. In particular, the cyclic oligopeptide of the invention is of the formula: (A) (SEQ ID NO:2) where one of $AA^1$ or $AA^6$ is an amino acid having a carboxylic acid side-chain and the other is a carboxylic acid having an amine functional group on the side-chain such that $X^1$ and $X^2$ together form an amide bond; and each of $AA^2$-$AA^5$ and $AA^7$-$AA^{11}$ is independently natural or unnatural amino acids with at least one, typically at least two, often at least three, more often at least four, and most often at least five of which is an amino acid that is present in the corresponding position of oxytocin.

15 Claims, 11 Drawing Sheets

Specification includes a Sequence Listing.

Oxytocin (SEQ ID NO:1)

| | EC50 (nM) | |
|---|---|---|
| | OTR | MOR |
| Oxytocin | 2.3 ± 1.7 | |
| 2LS 118-1 | 3760 ± 3123 | NA |
| 2LS118-2 | 7040 ± 2960 | NA |
| 2LS118-3 | NA | NA |
| 2LS118-4 | NA | NA |
| 2LS118-5 | NA | NA |
| 2LS118-6 | NA | NA |
| SS-Oxy 1 | 0.54 ± 0.48 | NA |
| SS-Oxy 2 | 161 ± 161 | NA |
| SS-Oxy 3 | 0.28 ± 0.17 | NA |
| SS-Oxy 4 | 0.73 ± 0.49 | NA |
| SS-Oxy 5 | 216 ± 109 | NA |
| SS-Oxy 6 | 0.06 ± 0.01 | NA |

OXYTOCIN ANALOGUES AND METHODS FOR USING THE SAME

CROSS-REFERENCE TO RELATED APPLICATIONS

This application claims the priority benefit of U.S. Provisional Application No. 63/056,930, filed Jul. 27, 2020, which is incorporated herein by reference in its entirety.

FIELD OF THE INVENTION

The present invention relates to cyclic oligopeptides and methods for using the same. The cyclic oligopeptides peptides of the invention may be considered as analogues of oxytocin ("OT") and arginine vasopressin ("AVP") where the labile disulfide linkage between two cysteine amino acids are replaced with a more stable amide bond. The cyclic oligopeptides of the invention can also include a glycoside (i.e., glycosylated cyclic oligopeptide or cyclic glycopeptide) to increase stability in vivo, and blood-brain barrier penetration.

BACKGROUND OF THE INVENTION

Opioid drugs like morphine, fentanyl and Oxycontin© are considered to be the gold standard for managing moderate-to-severe pain, and are often used to treat chronic pain as well. Unfortunately, these drugs are plagued with undesired side effects, particularly respiratory depression, GI effects, euphoria and sedation, and the use of these drugs can lead to opiate use disorder (OUD) and fatal overdose. Prescription rates and subsequent addiction, abuse, and hospital admissions for overdose have soared in the past 20 years for opioid drugs, with fentanyl-related abuse and overdose in particular skyrocketing since 2012. Many strategies have been developed to generate efficacious opioids with reduced addiction potential, such as biased ligands, multifunctional ligands, or endogenous peptide derivatives, but none have yet been translated to clinical use. This unsolved limitation of opioids illustrates the great medical need for alternative efficacious non-opioid analgesics.

An alternate pain modulatory system of great interest is the oxytocin (OT) neuronal network. Extensive research to date has shown that OT modulates pain. As shown in FIG. 1, oxytocin (SEQ ID NO:1) is a cyclic peptide with S—S linkage between two cysteine amino acid residues located at the 1- and the 6-position. Importantly, OT has been shown to inhibit nociceptive pathways in peripheral nerve terminals, in the spinal cord, and in diverse brain pain regulatory systems including the periaqueductal grey, the amygdala, and the anterior cingulate cortex. This pattern is similar to the opioid system, thus explaining the efficacy of OT in modulating pain. Interestingly, modulation of oxytocin receptor ("OXTR") using an OXTR agonist does not induce the side effects typical of opioid agonists. Opioid receptors and OXTR are neuropeptide receptors, thus given its activities, it is believed that OT can also be used to treat opioid addiction and other forms of substance abuse, including alcoholism. Furthermore, based on its activity it is believed that OXTR agonists can also be used as non-opioid analgesics. Unfortunately, due to the instability of the native disulfide linkage, OT is unsuitable for use as a drug. Moreover, OT cannot readily cross the blood-brain barrier (BBB). Thus, it is generally not well suited for use as a pharmaceutical. Recently, intranasal delivery of native OT has been reported. However, this intranasal delivery method is dependent on the trigeminal nerve as a conduit, and misses important sites of OT action in the spinal cord and periphery. While small molecule OXTR ligands have been developed, they have yet to advance to the clinic.

Accordingly, there is a need for OT analogues that are more stable and/or can readily cross the blood-brain barrier.

SUMMARY OF THE INVENTION

Some aspects of the invention provide cyclic oligopeptides that overcome these and other limitations and shortcomings of oxytocin. In particular, cyclic oligopeptides of the invention replace the labile disulfide linkage that is present in the oxytocin with an amide bond. This change in combination with glycosylation to enhance BBB penetration provides stable and brain-penetrant OT agonists for use as drugs. In some embodiments, glycosylated cyclic oligopeptides of the invention provide increased BBB penetration and enhanced efficacy against pain (nociception) and other clinical conditions. Cyclic oligopeptides of the invention have been shown to target multiple G protein-coupled receptors (GPCRs) and can be used to treat a variety of clinical conditions such as, but not limited to, a chronic or acute pain, opioid addiction (i.e., opiate use disorder, OUD), substance use disorder (SUD), alcoholism (i.e., alcohol use disorder, AUD), Autism Spectrum Disorders, Asperger's Syndrome, and Social Anxiety Disorders, as well as other clinical conditions associated with neuropeptide receptor activities.

In some embodiments, the cyclic oligopeptides of the invention activate the OT receptor with high efficacy. Some cyclic oligopeptides of the invention have efficacious antinociceptive activity in animal models of acute pain, especially when compared to the native OT peptide which had no effect in vivo. Yet in other embodiments, cyclic oligopeptides of the invention are used to treat chronic pain, e.g., chemotherapy-induced peripheral neuropathy (CIPN). Unlike conventional OT based oligopeptides, some cyclic oligopeptides (e.g., glycosylated cyclic oligopeptides or cyclic glycopeptides) of the invention are stable and can penetrate blood brain barrier. Furthermore, cyclic glycopeptides of the invention reduce or eliminates side-effects associated with opioids. Thus, in some embodiments cyclic oligopeptides of the invention are non-addictive and non-opioid analgesics.

In one particular embodiment, the cyclic oligopeptide of the invention is of the formula:

Formula A (SEQ ID NO: 2)

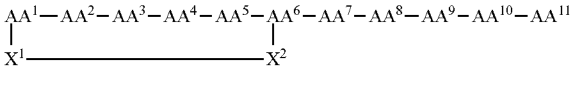

where one of AA or AA is an amino acid having a carboxylic acid side-chain and the other is a carboxylic acid having an amine functional group on the side-chain such that $X^1$ and $X^2$ together form an amide bond (i.e., a moiety of the formula: —NH—C(═O)— or —C(═O)—NH—); each of $AA^2$-$AA^5$ and $AA^7$-$AA^{11}$ is independently natural or unnatural amino acids with at least one, typically at least two, often at least three, more often at least four, and most often at least five of which is an amino acid that is present in the corresponding position of oxytocin; $AA^9$ and $AA^{10}$ can optionally be absent; and optionally at least one amino acid residues is glycosylated (i.e., attached or linked to a saccharide). In some embodiments, at least one, typically at least two, often at least three, more often at least four, and most often all of $AA^2$, $AA^4$, $AA^5$, and $AA^7$ are same amino acid residue as the corresponding position of oxytocin.

Still in other embodiments, at least one of $AA^9$ and $AA^{10}$ is absent. In other embodiments, both $AA^9$ and $AA^{10}$ are absent.

Yet in other embodiments, at least one amino acid residue is glycosylated. In further embodiments, at least amino acid residues are glycosylated.

In some embodiments, at least one of $AA^{10}$ and $AA^{11}$ is glycine and the other is serine, which is optionally glycosylated. Yet in other embodiments, both $AA^{10}$ and $AA^{11}$ are serine, each of which is independently optionally glycosylated.

In one particular embodiment, the cyclic oligopeptide of the invention is of the formula:

Formula I (SEQ ID NO:3)

$$\begin{array}{l} AA^1-Tyr-AA^3-Gln-Asn-AA^6-Pro-AA^8-AA^9-AA^{10}-AA^{11} \\ \;| \qquad\qquad\qquad\qquad\qquad\;\; | \\ X^1 \text{———————————} X^2 \end{array}$$

where $AA^1$, $AA^3$, $AA^6$, $AA^8$-$AA^{11}$, $X^1$, and $X^2$ are those defined herein. In some embodiments, each of $AA^9$ and $AA^{10}$ is independently Gly, Ser, cysteine, threonine or an analog thereof, or absent. Still in other embodiments, $AA^{11}$ is Gly, Ser, cysteine, threonine or an analog thereof.

Another aspect of the invention provides a method for treating a chronic or acute pain, opioid addiction, alcohol addiction, Autism Spectrum Disorders, Asperger's Syndrome, Social Anxiety Disorder, or a combination thereof, said method comprising administering a therapeutically effective amount of a cyclic oligopeptide to a subject in need of such a treatment, wherein said cyclic oligopeptide is of Formula A or a pharmaceutically acceptable salt thereof, a prodrug thereof, or a solvate thereof. In some embodiments, the method involves administration of cyclic oligonucleotide of Formula I or a pharmaceutically acceptable salt thereof, a prodrug thereof, or a solvate thereof. For the sake of clarity and brevity, whenever compound of Formula A and/or I are discussed, the scope of the invention includes a pharmaceutically acceptable salt thereof, a prodrug thereof, or a solvate thereof. In fact, throughout this disclosure in the absence of any conflict or limitations, all references to compound of Formula A also applies to compound of Formula I and vice versa.

DETAILED DESCRIPTION OF THE INVENTION

Figure 1:
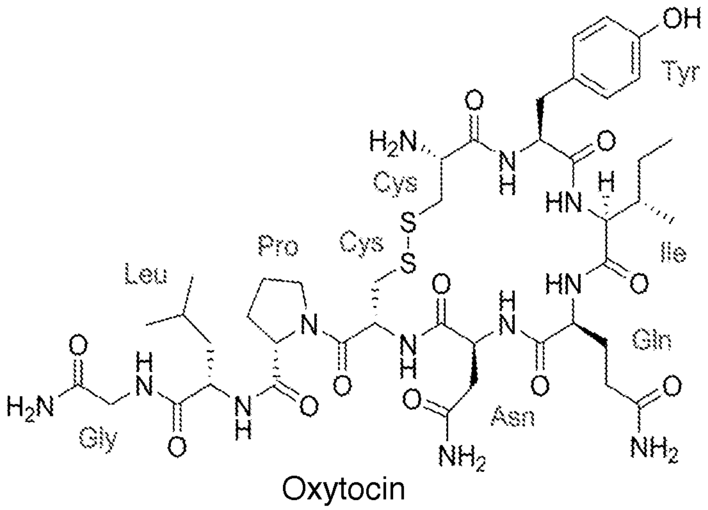
FIG. 1 shows chemical structure of oxytocin (SEQ ID NO:1).

Acute and chronic pain is a significant health and social problem in the United States and worldwide. Chronic pain affects nearly ⅓ of the population of the US and management of acute pain is a significant healthcare concern. Acute and chronic pain can significantly degrade daily function and quality of life, which adds a human cost to the social and economic costs. In general, less efficacious pain drugs are suitable for only some types of pain or limited patient population. For moderate-to-severe pain, opioid drugs like morphine are often the only efficacious option despite the risk of addiction and overdose.

While opioid drugs are efficacious for moderate to severe acute and cancer pain, their use for the treatment of chronic non-malignant pain is still in doubt. For instance, opioids are often not effective for managing neuropathic pain, and may not be efficacious in musculo-skeletal pain. Chronic opioid use can also paradoxically drive hyperalgesia and pain, termed opioid-induced hyperalgesia. In addition, opioid use, especially chronic use, is associated with the development of a constellation of negative side effects. These include tolerance, constipation, respiratory depression, dependence, and addiction. Escalating doses to maintain analgesic efficacy due to tolerance leads to the development of other side effects. Opioid addiction is also a major health, social, and political problem, with opioids accounting for 6 of the top 10 overdose drugs, with overdose rates rapidly rising over the last few years (e.g. the fentanyl overdose rate doubled from 2013-2014). Overall, these limitations reduce the potential clinical utility of opioid drugs, and further decrease the quality of life for patients. These limitations, especially the spiraling addiction crisis fueled by the extensive use of opiates, have spurred the search for alternative non-opioid analgesic drugs.

Some aspects of the invention are based on the oxytocin (OT) neuromodulatory system. The analgesic properties of endogenous OT have been known since the 1980's, and this neuronal network has come into a sharper focus for the treatment of pain. The principal location of OT cell bodies in the brain is the paraventricular nucleus (PVN) of the hypothalamus, which sends projections to multiple locations within the brain. These locations include crucial pain modulatory regions such as the anterior cingulate cortex, the amygdala, and the rostro ventromedial medulla. Furthermore, OT receptors and neuropeptides have been found in the dorsal horn of the spinal cord, another crucial pain regulatory region, and in the receptive fields of the skin. This neuroanatomical distribution explains the role of OT in pain modulation, and indeed studies have conclusively demonstrated the use of exogenous or endogenous OT stimulation to produce anti-nociceptive effects in multiple pain states. In addition, studies with OT ligands have shown that typical opioid side effects like constipation, and most importantly reward/addiction, are not induced, greatly increasing the promise and impact of OT ligands for effective pain management. In addition, the structure of OT is highly conserved among placental mammals, and the same circuitry has been identified in humans, primates, and rodents, suggesting that developing OT ligands in rodents should translate well to humans.

One of the principal limitations of developing OT ligands for pain (or other conditions) is the lack of stable ligands that can be delivered systemically to achieve sufficient levels of the drug in the brain. While many studies have demonstrated robust antinociception/analgesia with OT, these studies generally involve icv administration. Most clinical studies to date are performed with native oxytocin peptide delivered intranasally. This is problematic since the native peptide has a very short half-life due to a labile disulfide linkage and is also unable to cross the blood-brain barrier (BBB). The chemical structure of oxytocin is shown below. As can be seen below, a disulfide linkage is formed between two cysteine units at positions 1 and 6. In addition, the glycine unit is terminated at the carboxylic acid position as an amide. While intranasal administration does circumvent some of these difficulties, administering drug this way will miss important OT sites of action in the spinal cord and periphery, and furthermore, intranasal delivery is inherently more variable than other routes of administration. While a small number of non-peptide OT ligands have been developed, none of these ligands have passed pre-clinical studies, indicating that human translation with this class of ligand is highly uncertain, while the native peptide has demonstrated efficacy in humans.

The present invention solves these shortcomings by replacement of the labile disulfide linkage that is present between two cysteine amino acids (1→6) in OT with more stable amide bond.

In particular, some aspects of the invention provide a cyclic oligopeptide of the formula:

Formula A (SEQ ID NO:2)

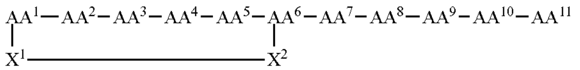

or a derivative thereof, where one of $AA^1$ or $AA^6$ is an amino acid having a carboxylic acid side-chain and the other is a carboxylic acid having an amine functional group on the side-chain such that $X^1$ and $X^2$ together form an amide bond, i.e., a moiety of the formula: —NH—C(═O)— or —C(═O)—NH—; and each of $AA^2$-$AA^5$ and $AA^7$-$AA^{11}$ is independently natural or unnatural amino acids with at least one, typically at least two, often at least three, more often at least four, and most often at least five of which is an amino acid that is present in the corresponding position of oxytocin. In addition, each of $AA^9$ and $AA^{10}$ can independently optionally be absent. Moreover, $AA^{11}$ can be terminated as an amide, a free carboxylic acid or an ester. In one particular embodiment, the cyclic oligopeptide of the invention is of the formula:

Formula I (SEQ ID NO:3)

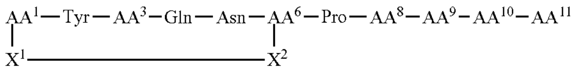

or a derivative thereof, where $AA^1$, $AA^3$, $AA^6$, $AA^9$-$AA^{11}$, $X^1$, and $X^2$ are those defined herein. As used herein, the terms "those defined above" and "those defined herein" when referring to a variable incorporates by reference the broad definition of the variable as well as narrower definition(s), if any. In some embodiments, each of $AA^9$ and $AA^{10}$ is independently Gly, Ser, cysteine, threonine or an analog thereof, or absent. Still in other embodiments, $AA^{11}$ is Gly, Ser, cysteine, threonine or an analog thereof.

Analogs of threonine are typically of the formula:

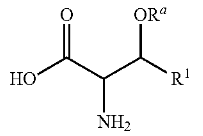

where Ra is H, alkyl, or a saccharide, and $R^1$ is alkyl. The term “alkyl” refers to a saturated linear monovalent hydrocarbon moiety. Unless the number of carbon atoms is specified, the term “alkyl” typically refers to hydrocarbon moiety having one to twenty, typically one to twelve, often one to ten, and more often one to six carbon atoms or a saturated branched monovalent hydrocarbon moiety of three to twenty, typically three to twelve, often three to ten, and more often three to six carbon atoms. Exemplary alkyl group include, but are not limited to, methyl, ethyl, n-propyl, 2-propyl, tert-butyl, n-pentyl, neopentyl, dodecyl, and the like. Still in other embodiments, threonine analogs are of the formula:

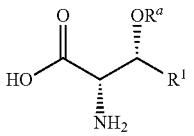

However, it should be appreciated other isomers, including allo-threonine, are within the scope of the invention. Analogs of threonines can be readily prepared using methods known to one skilled in the art. See, for example, *JOC,* 2001, 66, pp. 7178-7183, which is incorporated herein by reference in its entirety.

Natural amino acids are well known to one skilled in the art and refers to the 20 proteinogenic amino acids. Unnatural amino acids refer to non-proteinogenic amino acids that either occur naturally or are chemically synthesized. Some examples of unnatural amino acids can be found at sigmaaldrich.com/chemistry/chemistry-products.html?TablePage=16274965, see also, en.wikipedia.org/wiki/Non-proteinogenic_amino_acids, both of which are incorporated herein by reference in their entirety.

It should be appreciated that the scope of the invention includes retro modified cyclic oligopeptide of Formula A. The term “retro modified” refers to a peptide which is made up of L-amino acids in which the amino acid residues are assembled in opposite direction to the native peptide with respect the which it is retro modified. The scope of the invention also includes inverso modified cyclic oligopeptide of Formulas A. The term “inverso modified” refers to a peptide which is made up of D-amino acids in which the amino acid residues are assembled in the same direction as the native peptide with respect to which it is inverso modified. Furthermore, the scope of the invention also includes retro-inverso modified cyclic oligopeptide of Formulas A. The term “retro-inverso modified” refers to a peptide which is made up of D-amino acids in which the amino acid residues are assembled in the opposite direction to the native peptide with respect to which it is retro-inverso modified. Still further, the scope of the invention also includes cyclic oligopeptide of Formulas A where a mixture of (L)- and (D)-isomers of $AA^1$-$AA^{11}$ is present.

It should also be appreciated that one or more of the amino acids in cyclic oligopeptide of Formulas A can be replaced with an equivalent amino acid, for example, L (leucine) can be replaced with isoleucine or other hydrophobic side-chain amino acid such as alanine, valine, methionine, etc., and amino acids with polar uncharged side chain can be replaced with other polar uncharged side chain amino acids. In addition, a derivative of cyclic oligopeptides of the invention can also be used in methods and compositions of the invention. The term “derivative” refers to (i) any chemical modification of the amino acid, such as alkylation (e.g., methylation, ethylation or benzylation) of the amino group or functional group on the side chain, removal of the side-chain functional group, etc. (e.g., conversion of —OH, —SH—, or —$NH_2$ to H), and/or (ii) conservative substitutions of amino acid. As used herein, the term “conservative substitutions of amino acid” refers to replacing an amino acid with another amino acid having a similar side-chain functional group. For example, basic amino acids that can be replaced or substituted by one another include arginine, lysine and histidine. Acidic amino acids that can be replaced or substituted by one another include glutamic acid and aspartic acid. Polar amino acids that can be replaced or substituted by one another include glutamine and asparagine. Hydrophobic amino acids that can be replaced or substituted by one another include leucine, isoleucine and valine. Aromatic amino acids that can be replaced or substituted by one another include phenylalanine, tryptophan and tyrosine. Small amino acids that can be replaced or substituted by one another include glycine, alanine, serine, threonine and methionine. As can be seen, subgroups of amino acids are based on the characteristics of side-chain of the amino acid. More detailed subgroups of amino acids are: (1) Aliphatic—alanine, glycine, isoleucine, leucine, proline, valine; (2) Aromatic—phenylalanine, tryptophan, tyrosine; (3) Acidic—aspartic acid, glutamic acid; (4) Basic—arginine, histidine, lysine; (5) Hydroxylic—serine, threonine; (6) Sulphur-containing—cysteine, methionine; and (7) Amidic (containing amide group)—asparagine, glutamine. In general, amino acid substitutions that do not generally alter specific activity are known in the art and are described, for example, by H. Neurath and R. L. Hill, 1979, in “The Proteins,” Academic Press, New York. Some of the exemplary common amino acid substitutions include, but are not limited to, Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

The terminal amino acid residue of cyclic oligopeptides of the invention (i.e., $AA^{11}$) can be present as a carboxylic acid moiety, an amide moiety (which includes mono- and di-alkylated amides), an ester, or other carboxylate derivative.

Yet in other embodiments, one or more amino acid residues is a (D)-isomer. In one particular embodiment, at least one, typically at least two, and often at least three amino acid residue of Formula I are (D)-isomer amino acid residue.

In some embodiments, $AA^2$ is an aromatic amino acid. Yet in other embodiments, $AA^4$ is an acidic amino acid. Still in other embodiments, $AA^5$ is a polar amino acid. In further embodiments, $AA^7$ is proline.

Still in one particular embodiment, the cyclic oligopeptide of the invention is of Formula I, where one of $AA^1$ or $AA^6$ is an amino acid having a carboxylic acid side-chain and the other is a carboxylic acid having an amine functional group on the side-chain such that $X^1$ and $X^2$ together form an amide bond (i.e., a moiety of the formula: —NH—C(═O)— or —C(═O)—NH—); $AA^3$ is Phe or Ile; $AA^8$ is Arg, Leu, or Aib; $AA^9$ is Gly or absent; $AA^{10}$ is Gly, Ser, or absent; and $AA^{11}$ is Gly or Ser that is terminated as an amide, a free carboxylic acid, or an ester (e.g., methyl, ethyl, t-butyl, iso-propyl, etc.).

In some embodiments, one of $AA^1$ and $AA^6$ comprises aspartate or glutamate and the other comprises lysine, ornithine, diaminobutyric acid (DABA), or 2,3-diaminopropionic acid (DAPA or Dap). As can be appreciated, depending on the amino acid of AA1 and/or AA6 the ring size of the cyclic peptide can be modified.

Still in other embodiments, at least one of the amino acid moieties of the cyclic oligopeptides of the invention is glycosylated. As used herein, the "glycosylated" refers to having a carbohydrate moiety. The terms "sugar" and "carbohydrate" are used interchangeably herein and generally refers to a mono- and/or disaccharide. The term "monosaccharide" refers to any type of hexose of the formula $C_6H_{12}O_6$ or a derivative thereof. The ring structure (i.e., ring type) of the monosaccharide can be a pyranose or a furanose. In addition, the monosaccharides can be an α- or β-anomer. Monosaccharide can be a ketonic monosaccharide (i.e., ketose), an aldehyde monosaccharide (i.e., aldose), or any type of hexose of the formula $C_6H_{12}O_6$ or a derivative thereof. Exemplary aldoses of the invention include, but are not limited to, allose, altrose, glucose, mannose, gulose, idose, galactose, talose, ribose, arabinose, xylose, lyxose, and derivatives thereof. Exemplary ketoses of the invention include, but are not limited to, psicose, fructose, sorbose, tagatose, ribulose, xylulose, and derivatives thereof. As used herein the term "derivative" refers to a derivative of a monosaccharide in which one or more of the hydroxyl groups is replaced with hydrogen (e.g., 2-deoxy glucose, 5-deoxyglucose, etc.), an amine (e.g., amino sugars) or is replaced with a halogen, such as chloro, fluoro or iodo, (e.g., 5-fluoroglucose, 2-fluoroglucose, 5-chrologlucose, 2-chloroglucose, etc.), or a nitrogen (e.g. glucosamine, N-acetylglucosamine). Monosaccharide can be an (L)-isomer or a (D)-isomer. The term "disaccharide" refers to a carbohydrate composed of two monosaccharides. It is formed when two monosaccharides are covalently linked to form a dimer. The linkage can be a (1→4) bond, a (1→6) bond, a (1→2) bond, etc. between the two monosaccharides. In addition, each of the monosaccharides can be independently an α- or β-anomer. Exemplary disaccharides that can be used in the present invention include, but are not limited to, sucrose, lactose, maltose, trehalose, cellobiose, melibiose, lactulose, and chitobiose, etc. Each of the monosaccharides can independently be a ketonic monosaccharide (i.e., ketose), an aldehyde monosaccharide (i.e., aldose), or any type of hexose of the formula $C_6H_{12}O_6$ or a derivative thereof. Exemplary aldoses that can be used in preparing disaccharides of the invention include, but are not limited to, allose, altrose, glucose, mannose, gulose, idose, galactose, talose, ribose, arabinose, xylose, lyxose, and derivatives thereof. Exemplary ketoses that can be used in preparing disaccharides of the invention include, but are not limited to, psicose, fructose, sorbose, tagatose, ribulose, xylulose, and derivatives thereof. Each monosaccharide unit within the disaccharide can also be independently an (L)-isomer or a (D)-isomer.

Yet in other embodiments, the cyclic oligopeptide is glycosylated with a monosaccharide or a disaccharide. In one particular embodiment, the cyclic oligopeptide comprises a monosaccharide, such as allose, altrose, glucose, mannose, gulose, idose, galactose, talose, ribose, arabinose, xylose, lyxose, psicose, fructose, sorbose, tagatose, ribulose, or xylulose. In another embodiment, the cyclic oligopeptide is substituted with a disaccharide, such as sucrose, lactose, maltose, trehalose, cellobiose, lactulose, chitobiose, allose, altrose, glucose, mannose, gulose, idose, galactose, talose, ribose, arabinose, xylose, lyxose, psicose, fructose, sorbose, tagatose, ribulose, or xylulose. Generally, when glycosylated a side-chain functional group of an amino acid residue of cyclic oligopeptide of the invention is glycosylated. Some of the amino acid residues that can be glycosylated include, but are not limited to, serine, threonine, allo-threonine, cysteine, etc.

In some embodiments, the monosaccharide is an (L)-isomer. Yet in other embodiments, the monosaccharide is a (D)-isomer.

Still in other embodiments, each of the monosaccharide unit of the disaccharide is independently an (L)- or a (D)-isomer.

In one particular embodiment, the glycosylated amino acid is serine, cysteine, threonine or an analog thereof. Still in other embodiments, the glycosylated amino acid is serine.

Glycosylation of cyclic oligopeptides provides a wide range of benefits such as increased water solubility and/or membrane hopping leading to increased drug transport across the BBB.

Unlike small organic molecule based OXTR agonists, cyclic oligopeptides of the invention have a significantly reduced or non-toxic metabolic profile as amino acids and sugars are the metabolites. Furthermore, because peptides in general have a high selectivity for the corresponding receptors, cyclic peptides, which are analogs of OT, have high selectivity for OXTR, thereby significantly reducing or even completely eliminating side-effects observed in small molecule based OXTR agonists. Because of these and other advantages compared to native OT and small molecule based OXTR agonists, cyclic peptides of the invention overcome various problems associated with using native OT or small molecules to modulate OXTR. In particular, cyclic peptides of the invention overcomes druggability issues with OT, and offers superior delivery an efficacious analgesic with none of the abuse and other undesired side-effects observed with opioid drugs.

As discussed herein, cyclic oligopeptides of the invention modulate a neuropeptide receptor, namely, oxytocin receptor ("OXTR"). Furthermore, some cyclic oligopeptides of the invention can also modulate other neuropeptide receptors, such as opioid receptors and other central nervous system (CNS) receptors. Accordingly, cyclic oligopeptides of the invention are useful in treating various clinical conditions associated with modulation of various neuropeptide receptors. In one particular embodiment, cyclic oligopeptides of the invention can be used to treat chronic or acute pain, opioid addiction, alcohol addiction, Autism Spectrum Disorders, Asperger's Syndrome, as well as other clinical conditions associated with neuropeptide receptor activities. The "biousian approach" of the present invention is superior to native OT peptide or small molecule as cyclic oligopeptides of the invention produce metabolites that are more regarded as nutrients (e.g., amino acids and sugars) rather than toxins. This feature, combined with the peptides' generally high receptor selectivity and potent efficacy, make cyclic oligopeptides of the invention, which are derivatives of endogenous neuropeptide peptide (e.g., OT), useful treatment of choice for clinical conditions associated with neuropeptide receptors. Because of the modularity of the peptide design, some cyclic oligopeptides of the invention have the ability to interact with 2 or more closely related receptors or offer selectivity of one receptor over another closely related receptor, e.g., OT vs arginine vasopressin ("AVP") receptors.

As discussed herein, some cyclic oligopeptides of the invention are glycopeptides comprising a cyclic oligopeptide and a carbohydrate. Glycopeptides are more stable metabolically and their persistence in vivo promotes penetration of the BBB, which allows for the resulting glycopeptides to function as brain-penetrant CNS drugs. Accordingly, some cyclic oligopeptides of the invention are useful as CNS drugs.

Some cyclic oligopeptides of the invention are stable, BBB-penetrant, OXTR-selective glycopeptides with high efficacy and low side effects in managing a clinical condition associated with a neuropeptide receptor, including managing acute and chronic pain. Selectivity (e.g., at the OXTR and AVP-1A/1B/2 receptors), affinity, potency, and efficacy of cyclic oligopeptides of the invention can be readily determined by using radioligand binding and a high throughput arrestin recruitment assay to measure receptor activation of human receptors expressed in cells.

In some embodiments, cyclic oligopeptides of the invention have affinity (i.e., Ki) for OXTR of about 100 nM or less, typically about 50 nM or less, and often about 10 nM or less. When referring to a numerical value, the terms "about" and "approximately" are used interchangeably herein and refer to being within an acceptable error range for the particular value as determined by one of ordinary skill in the art, which will depend in part on how the value is measured or determined, e.g., the limitations of the measurement system, i.e., the degree of precision required for a particular purpose. For example, the term "about" typically means within 1 standard deviation, per the practice in the art. Alternatively, the term "about" can mean±20%, typically ±10%, often ±5% and more often ±1% of the numerical value. In general, however, where particular values are described in the application and claims, unless otherwise stated, the term "about" means within an acceptable error range for the particular value.

Yet in other embodiments, cyclic oligopeptides of the invention have potency (i.e., $EC_{50}$) for modulation of OXTR of about 100 nM or less, typically about 50 nM or less, and often about 10 nM or less.

Still in other embodiments, cyclic oligopeptides of the invention have at least about 50 fold selectivity, typically at least about 100 fold selectivity, and often at least about 150 fold selectivity for OXTR versus 3 AVP receptors. This selectivity helps to avoid potential side effects resulting from AVP receptor activation, such as increases in blood pressure.

Pharmacokinetic ("PK") parameters of cyclic oligopeptides of the invention can be analyzed using any of the methods known to one skilled in the art. In one particular embodiment, PK parameters and BBB penetration of cyclic oligopeptides of the invention is determined using shotgun microdialysis and $MS^3$ measurement. This method is highly efficient, permitting in vivo analysis of all compounds by batch administration. This method thus allows generation of full SAR and STR information for cyclic oligopeptides of the invention.

In one particular embodiment, cyclic oligopeptides of the invention can maintain brain concentrations that can maximally activate the receptor (e.g., >10 nM) for a time period useful for pain management (>2 hrs). Still in other embodiments, cyclic oligopeptides of the invention have efficacy of at least about 75%, typically at least about 80%, and often about equal (i.e., 100%) or more compared to morphine. Yet in other embodiments, cyclic oligopeptides of the invention have about 50% or less, typically about 40% or less, and often about 25% or less side effects (either intensity or the total number of side effects) compared to morphine or arginine vasopressin ("AVP").

Some of the representative cyclic oligopeptides of the invention are shown in Table 1 below. It should be noted in all instances, a cyclic ring structure is formed between amino acids at positions 1 and 6.

TABLE 1

| Representative cyclic oligopeptides of the invention | |
|---|---|
| Cpd Code | all oligopeptides listed are cyclized oligopeptides (↱ $AA^1$-$AA^6$ ↰) |
| AVP | Cys-Tyr-Phe-Gln-Asn-Cys-Pro-Arg-Gly-$CONH_2$ (SEQ ID NO: 4) |
| OT | Cys-Tyr-Ile-Gln-Asn-Cys-Pro-Leu-Gly-$CONH_2$ (SEQ ID NO: 1) |
| 2LS118-1 | Asp-Tyr-Ile-Gln-Asn-Dap-Pro-Leu-Gly-$CONH_2$ (SEQ ID NO: 5) |
| 2LS118-2 | Glu-Tyr-Ile-Gln-Asn-Dap-Pro-Leu-Gly-$CONH_2$ (SEQ ID NO: 6) |
| 2LS118-3 | Dap-Tyr-Ile-Gln-Asn-Asp-Pro-Leu-Gly-$CONH_2$ (SEQ ID NO: 7) |
| 2LS118-4 | Asp-Tyr-Ile-Gln-Asn-Dap-Pro-Leu-SerGlc-$CONH_2$ (SEQ ID NO: 8) |
| 2LS118-5 | Asp-Tyr-Ile-Gln-Asn-Dap-Pro-Leu-Gly-SerGlc-$CONH_2$ (SEQ ID NO: 9) |
| 2LS118-6 | Asp-Tyr-Ile-Gln-Asn-Dap-Pro-Leu-Gly-(SerGlc)2-$CONH_2$ (SEQ ID NO: 10) |
| SSoxy1 | Asp-Tyr-Ile-Gln-Asn-Dap-Pro-Leu-SerLact-$CONH_2$ (SEQ ID NO: 11) |
| SSoxy2 | Asp-Tyr-Ile-Gln-Asn-Dap-Pro-Leu-Gly-SerLact-$CONH_2$ (SEQ ID NO: 12) |
| SSoxy3 | Asp-Tyr-Ile-Gln-Asn-Dap-Pro-Aib-SerGlc-$CONH_2$ (SEQ ID NO: 13) |
| SSoxy4 | Glu-Tyr-Ile-Gln-Asn-Dap-Pro-Leu-SerGlc-$CONH_2$ (SEQ ID NO: 14) |
| SSoxy5 | Glu-Tyr-Ile-Gln-Asn-Dap-Pro-Aib-SerGlc-$CONH_2$ (SEQ ID NO: 15) |
| SSoxy6 | Glu-Tyr-Ile-Gln-Asn-Dap-Pro-Aib-Gly-SerGlc-$CONH_2$ (SEQ ID NO: 16) |

Dap = 2,3-diaminopropionic acid ($HO_2C$-$CHNH_2$-$CH_2NH_2$); Aib = 2-Aminoisobutyric acid; Glc = glucose; and Lact = lactose The structure activity relationship ("SAR") that are known generally holds true for cyclic oligopeptides of the invention. For example, modifications of the $Tyr^2$ (e.g., from —OH to —$OCH_3$, —$CH_3$ or —$CH_2CH_3$) enhance binding to the OT receptor.

Cyclic oligopeptides can be prepared in solution or using a solid phase synthesis. One particular embodiment for producing cyclic oligopeptides of the invention is schematically illustrated in FIG. 2.

Figure 2:
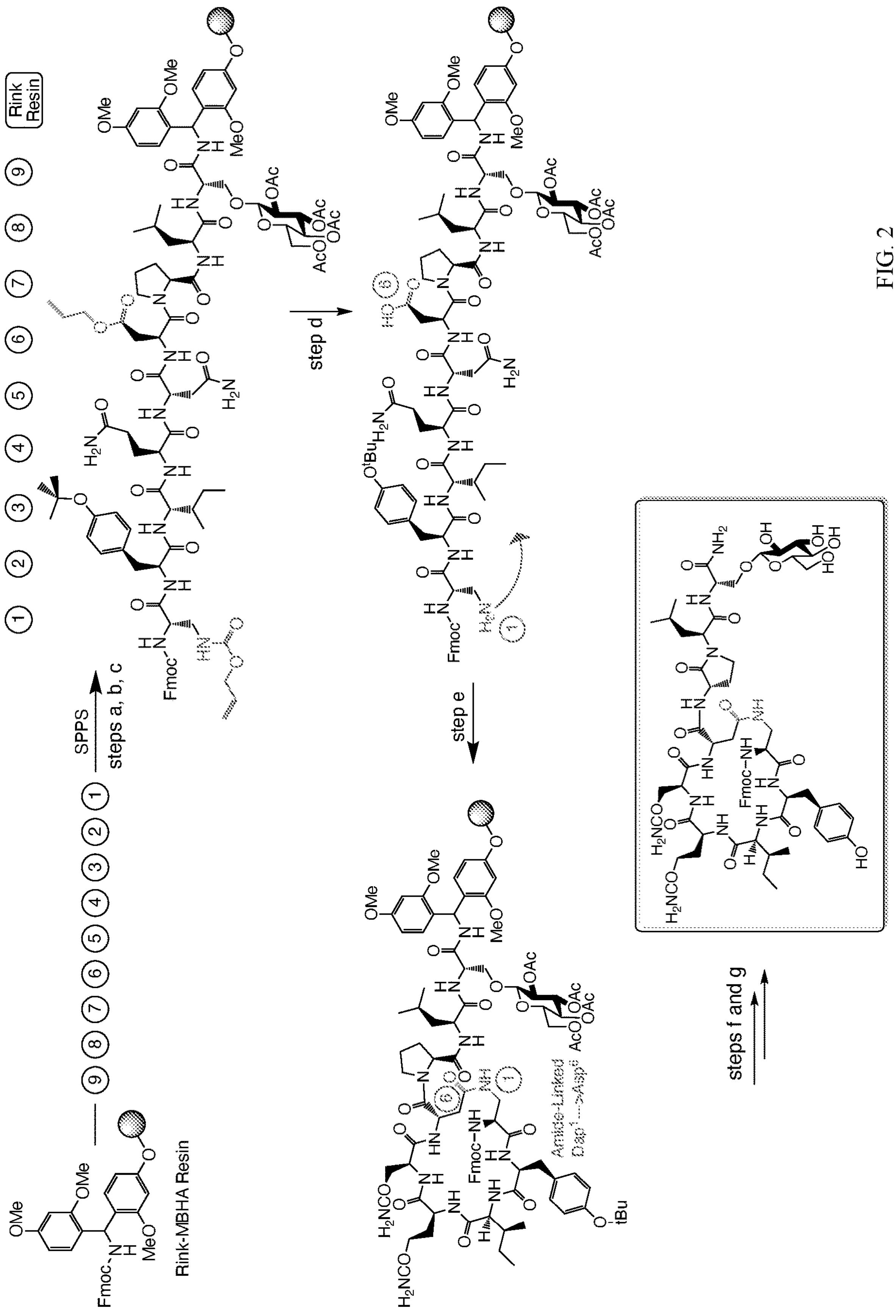
FIG. 2 is an illustration of one particular reaction scheme for synthesizing cyclic oligopeptides of the invention using Rink-MBHA resin.

Briefly, as shown in FIG. 2, Fmoc-based SPPS on Rink-MBHA resin produced protected linear nona-glycopeptides in high yield (steps a-c). Differential removal of the allylic protection at positions 1 and 6 by hydrogen atom transfer (step d), followed by cyclization on the resin with PyClock in NMP (step e), then acetate removal with hydrazine hydrate in methanol (step f), and finally cleavage from the resin with the TFA cocktail (step g) produced the cyclic oligopeptides of the invention. The cyclic OT analogues were purified by RP-HPLC on a Cis column using $CH_3CN$—$H_2O$ w/0.1% TFA.

One of the key advantages of cyclic oligopeptides of the invention is ability to selectively activate OXTR without any significant activation of MOR. In some embodiments, cyclic oligopeptides of the invention have the $EC_{50}$ for OXTR of about 1 mM or less, often about 500 nM or less, still more often about 100 nM or less, and most often about 10 nM or less. Yet in other embodiments, the Ki of cyclic oligopeptides of the invention for MOR is at least about 1000 nM or more, typically at least 2000 nM or more, and often at least about 2500 nM or more. In many instances, the selectivity of cyclic oligopeptides of the invention for OXTR compared to MOR is at least 100:1, typically at least 500:1, and often at least 1,000:1.

Without being bound by any theory, due to a high selectivity of OXTR compared to MOR, it is believed cyclic oligopeptides of the invention can be used in treating a variety of clinical conditions without inducing many of the side effects typical of opioid agonists. Accordingly, one particular example of using cyclic oligopeptides of the invention is in pain management, such as but not limited to, post-operative pain, chronic lower back pain, and post traumatic stress disorder ("PTSD"). One of the key advantages of cyclic oligopeptides of the invention is ability to provide pain relief similar to opioid based pain relief compounds, such as morphine, while also enhancing patient mental wellbeing and/or without resulting in addictive or other side-effects seen in opioid analog compounds. Other clinical conditions that can be treated with cyclic oligopeptides of the invention include, but are not limited to, chronic pain, acute pain, opioid addiction, alcohol addiction, Autism Spectrum Disorders, and Asperger's Syndrome.

In some embodiments, cyclic oligopeptides of the invention are glycosylated. In some embodiments, such cyclic glycopeptides show both enhanced serum half-life and enhanced BBB penetration when compared to un-glycosylated peptides. However, it should be appreciated that the scope of the invention is not limited to glycosylated cyclic oligopeptides. In fact, compared to oxytocin, all cyclic oligopeptides of the invention are more stable due to replacement of disulfide linkage with an amide linkage.

It has been shown that morphine's analgesic and addictive properties are abolished in mice lacking the mu-opioid receptor. This observation shows that mu-receptors mediate both the therapeutic and the adverse activities of morphine. In addition, a series of studies has shown that the reinforcing properties of alcohol, cannabinoids, and nicotine—each of which acts at a different receptor—are also strongly diminished in these mutant mice. The genetic approach therefore highlights mu-receptors as convergent molecular switches, which mediate reinforcement following direct (morphine) or indirect activation (non-opioid drugs of abuse. Endogenous opioid binding to mu-receptors has further shown to mediate natural rewards and has been proposed to be the basis of infant attachment behavior. Furthermore, it has been shown in mice lacking the mu-receptor gene a loss of morphine-induced analgesia, reward, and dependence; increased sensitivity to painful stimuli; reduced reward to non-opioid drugs of abuse; and altered emotional responses.

Because cyclic oligopeptides of the invention lack binding to mu-receptors (or MOR), it is believed cyclic oligopeptides of the invention also lack side-effects observed in opioid or non-opioid drugs that bind to MOR.

Administration and Pharmaceutical Composition

The present invention includes pharmaceutical compositions comprising at least one cyclic oligopeptide of the invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the cyclic oligopeptides of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the cyclic oligopeptide used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the cyclic oligopeptides of the invention.

Typically, cyclic oligopeptides of the invention are administered as pharmaceutical formulations including those suitable for oral (including buccal and sub-lingual), nasal, topical, pulmonary, or parenteral (including intramuscular, intraarterial, intrathecal, subcutaneous and intravenous) administration or in a form suitable for administration by inhalation or insufflation. Typical manner of administration is generally oral using a convenient daily dosage regimen which can be adjusted according to the degree of affliction.

A cyclic oligopeptide or cyclic oligopeptides of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active cyclic oligopeptides or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The cyclic oligopeptides of the invention can be formulated in a wide variety of oral administration dosage forms. The pharmaceutical compositions and dosage forms can comprise a cyclic oligopeptide or cyclic oligopeptides of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active cyclic oligopeptide. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active cyclic oligopeptide with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The cyclic oligopeptides of the invention can also be formulated for parenteral administration (e.g., by injection; bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The cyclic oligopeptides of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The cyclic oligopeptides of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The cyclic oligopeptides of the invention can be formulated for aerosol administration, particularly to the respiratory tract and including intranasal administration. The cyclic oligopeptide will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively, the active ingredients can be provided in a form of a dry powder, for example, a powder mix of the cyclic oligopeptide in a suitable powder base such as lactose, trehalose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the cyclic oligopeptides of the invention can be formulated in transdermal or subcutaneous drug delivery devices. These delivery systems are advantageous when sustained release of the cyclic oligopeptide is necessary or desired and when patient compliance with a treatment regimen is crucial. Cyclic oligopeptides in transdermal delivery systems are frequently attached to a skin-adhesive solid support. The cyclic oligopeptide of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the cyclic oligopeptide in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a cyclic oligopeptide of Formula (I), as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of cyclic oligopeptides of Formula (A) or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The cyclic oligopeptides of Formula (A) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a cyclic oligopeptide of Formula (A), or a pharmaceutically acceptable salt thereof or a prodrug thereof, with one or more pharmaceutically acceptable carriers, diluents, or excipients.

When the compositions of this disclosure comprise a combination of a cyclic oligopeptide of the present disclosure and one or more additional therapeutic or prophylactic agent, both the cyclic oligopeptide and the additional agent are usually present at dosage levels of between about 10 to 150%, and more typically between about 10 and 80% of the dosage normally administered in a monotherapy regimen.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1. Synthesis and Pharmacokinetics

The synthetic approach to the amide-linked analogues is shown in Scheme 1. The allyloxy-protection is used on the amine and carboxylate side chains, which can be removed while the peptide chain is still on the resin, and then cyclized to form the cyclic ring. Following this closure, the SPPS assembly is completed. Inverting the amide bond direction (e.g., $Asp^1 \rightarrow Dap^6$ vs $Dap^1 \leftarrow Asp^6$) suggested that the later amide direction reduce binding to OXTR by two log units. Changing the size of the ring (e.g., Asp vs Glu, Dap vs Dab) can alter OXTR vs AVP receptor binding. The ring can be further expanded or increased in size using Ornithine (5 carbons) and Lysine (6 carbons). Lipophilicity can be added to enhance membrane interactions without interfering with binding to OXTR.

The term "biousian behavior" is used to rationalize the transport properties of the glycopeptides. Basically, this describes the fact that the molecular conformations of glycosylated amphipathic peptides are quite different in solution vs the more limited conformational ensemble seen in the presence of biological membranes. Endogenous peptide neurotransmitters are highly amphipathic and will reside in a membrane environment, precluding transport and BBB penetration. Glycosylation "pulls" the resulting glycopeptide away from the membrane long enough to "hop" to another membrane. Increasing glycosylation increases the distance of the hops. Without being bound by any theory, it is believed that BBB penetration is facilitated by endocytosis (transcytosis) and that as the degree of glycosylation is increased, BBB penetration increases to a maximum level and then decreases as water solubility of the glycoside starts to interfere with membrane binding. This observation shows there is an "optimal level" of glycosylation for transport and BBB penetration.

Peptide Sequence. It is believed that one of the most important positions in differentiating OXTR and AVP receptor agonism is position 8, favoring OXTR binding with a lipophilic amino acid (e.g. $Leu^8$) and AVP receptor binding with a basic amino acid (e.g. $Arg^8$). Note that the presence of a single basic residue at position 8 (Leu→Lys→Arg) promotes strong activity at the AVP receptors. Some sequence modifications leads to enhanced OXTR selectivity.

Incorporation of a water-soluble sugar moiety into cyclic oligopeptide shifts the equilibrium away from the membrane, and allows the glycopeptide to be rapidly distributed throughout the body. Effects of glycosylation on various properties (e.g., activity, selectivity, efficacy, PK parameters, etc.) is studied, for example, by replacing $Gly^9$ with the $Ser^9$-Glc vs appending the glucoside as a Serio-Glc. See Table 1. Some cyclic oligopeptides of the invention include two glycosides. See Table 1. In general, having more than one site of glycosylation lead to increased water solubility. The optimal location of the glycoside can be readily determined by using the procedures disclosed herein. In some embodiments, the glycoside is located at or near (i.e., within 2 or 3 amino acid position of) the C-terminus of the cyclic oligopeptide. It has been found, however, that the presence of a glycoside at the N-terminus does not significantly interfere with binding or the activity of the cyclic oligopeptides of the invention.

Example 2. Molecular Pharmacology at the OT, $AVP_{1a}$, $AVP_{1b}$ and $AVP_2$ Receptors In vitro screening of cyclic peptides of the invention for their molecular pharmacology at target receptors expressed in cell lines permits rapid and efficient screening of compounds of greatest interest. Since OXTR and the 3 AVP receptors couple to different Ga subtypes, an assay like $^{35}S$-GTPγS coupling or cAMP accumulation cannot be used for all 4 receptors. In order to use the same assay for all 4 receptors, minimizing inter-assay variability, both radioligand binding and a high-throughput arrestin recruitment assay from DiscoveRx was chosen. All 4 cell lines are available commercially from DiscoveRx, and the OT cell line is in hand, and was used to generate data on compounds listed in Table 1. This approach permits rapid and efficient analysis of affinity (Ki), potency ($EC_{50}$), efficacy ($E_{MAX}$), and selectivity at all 4 receptors.

The 3 AVP lines are purchased from DiscoveRx, while the OT line is in hand. Each of the 4 cell lines are tested with concentration curves with OT cell lines and AVP cell lines as positive controls. Vehicle treatment are used as a negative control. Radioligand binding protocol with $^3$H-OT is used as the radioligand (PerkinElmer), while the arrestin recruitment assay is performed using the manufacturer's standard protocol. The data are acquired using a Microbeta2 scintillation counter (binding) or a BioTek Synergy multi-mode plate reader (arrestin), and the data analyzed by normalization to OT/AVP positive control and curve fitting using GraphPad Prism. This returns the affinity, potency, and efficacy values at each receptor. Positive controls: native OT and AVP peptides; Negative controls: vehicle, testing in parental cells.

Data demonstrates that some cyclic oligopeptides retain strong OT receptor potency, and some also have the same intrinsic anti-nociceptive activity as native OT peptide at the same dose in mice. This suggests that glycosylation does not substantially alter the molecular pharmacology of cyclic peptides of the invention.

Alternatively, a mix of assays appropriate for each Ga subtype, such as $^5$S-GTPγS coupling (Gai), cAMP accumulation (Gai and Gas), or calcium imaging ($G\alpha_q$) can be utilized. While comparing mismatched assays is not ideal, error can be minimized by normalizing within each assay to the performance of native OT/AVP positive control peptides.

Example 3. Measure In Vitro & In Vivo Stability and BBB Penetration of the Derivatives by Shotgun Microdialysis Studies have shown that glycosylation of peptides can retard degradation by hindering peptidases, and can lead to improved BBB penetration. The present inventors have developed an in vitro method for screening the stability of peptides in a biological solution. The present inventors have also developed an in vivo method using dual microdialysis and blood draws to measure the penetration of compounds across the BBB and to monitor the lifetime of compounds in the blood and in the cerebrospinal fluid (CSF). Using these procedures, compounds with and without glycosylation are examined in parallel and their behavior under these conditions are compared. This comparison allows directly measure the time-course of BBB penetration and PK/PD of the peptides and glycopeptides.

"Shotgun microdialysis" for direct comparison of in vivo lifetime and BBB penetration of peptide derivatives. In order to assess the effect of glycosylation on in vivo stability and BBB penetration, a method was developed that involves the co-injection of compounds and the quantitation of their concentration in the blood and in the CSF over time. A common challenge in animal research is inter-animal variability. Different animals often have slightly different responses to the same treatment, therefore it is often challenging to compare the behavioral or chemical responses of multiple animals to different drugs. A method, coined "shotgun microdialysis", was developed in which a single animal with multiple compounds of interest was injected and monitored the CSF concentrations using microdialysis. This allows direct comparison of the compounds within a single animal, and account for the variability between animals.

In microdialysis, a probe is surgically implanted into the target region (in this case the striatum). The probe has a semi-permeable membrane with a molecular weight cut-off. Perfusate is flowed through the probe, and species in the surrounding matrix can diffuse through the membrane as a function of the concentration gradient. Microdialysis allows for sampling from a region without altering the volume of that region, which is of particular relevance when studying the CSF.

Figure 3:
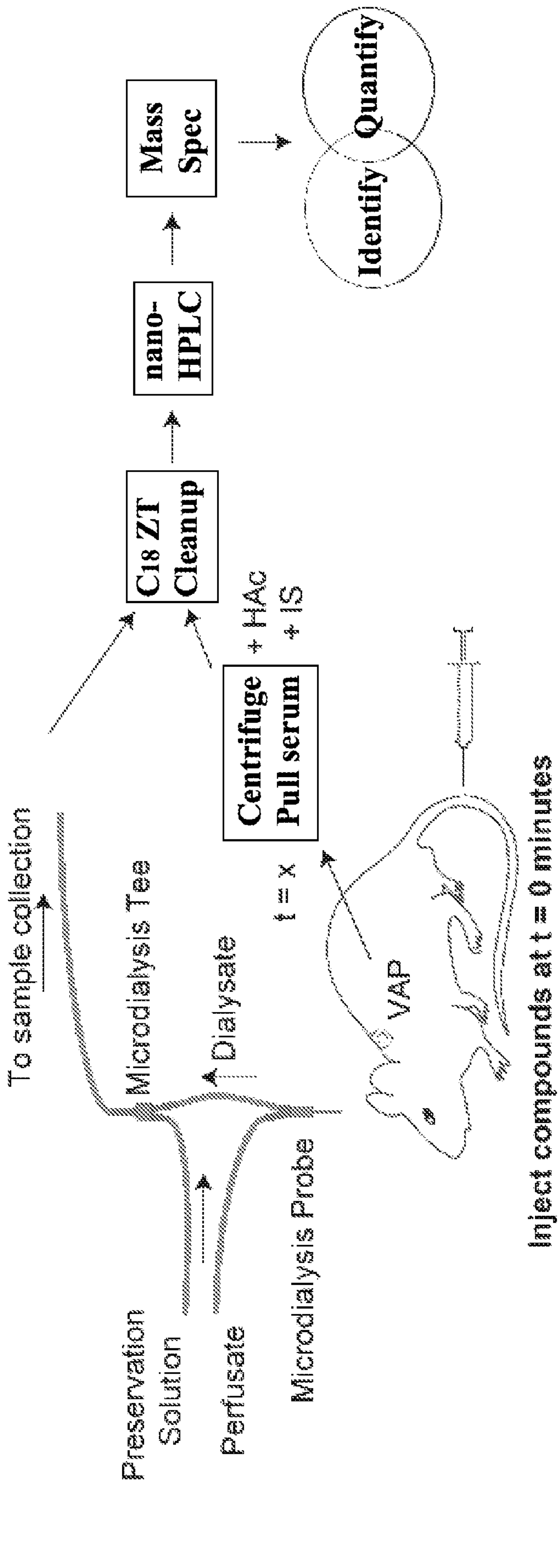
FIG. 3 is a schematic illustration showing workflow for collection and analysis of in vivo samples. Animals are surgically implanted with a vascular access port (VAP) for access to the carotid artery, and a microdialysis probe in the striatum. Animals are injected with a cocktail of 3.0 mg/kg of each compound in saline. Time-locked blood and dialysate samples are collected, normalized to the time of injection as t=0. aCSF, isotonic with the brain environment, is used as perfusate for microdialysis. A preservation solution comprised of 10% acetic acid, 140 pM DADLE (internal standard), and 2% acetonitrile in water (v/v) is coupled to the dialysate immediately using a microdialysis tee. Dialysate is stored on dry ice until analysis. Serum samples are collected by drawing 10 μL of whole blood through the VAP and centrifuging to separate out the serum. Serum samples are spiked with acetic acid and internal standard before freezing. Both types of samples go through the same preparation steps immediately prior to analysis, including ZipTip® cleanup. Samples are then analyzed with nano-LC-$MS^3$ and identified fragment peaks are used for quantification.

The work flow for in vivo experiments is shown in FIG. 3. Briefly, animals are injected intravenously with the target compounds at 3.0 mg/kg via tail vein injection. Blood draws are taken at t=−10, 1, 5, 10, 20, 30, 40, 50, 60, 70, 80, and 90 minutes (where t=0 corresponds to injection). Microdialysis fractions are time-locked with blood draws at ten-minute increments such that blood draws correlate with the median time of the microdialysis fraction. Blood draws are centrifuged for 2 minutes in a tabletop mini-centrifuge to separate the serum and the red blood cells. Serum is pulled off and diluted 100× into a solution of 50:50 aCSF "preservation solution" for matrix matching with the dialysate and standards, and immediately frozen on dry ice. Dialysate samples are collected for 10 minutes at a flow rate of 0.5 μL/min, with the microdialysis tee coupling a line containing preservation solution to the dialysate line immediately behind the probe, leading to a solution volume of 10 μL after 10 minutes. The dialysate samples are immediately frozen on dry ice.

All samples are desalted using μ-$C_{18}$ Zip Tips® (EMD Millipore) yielding a final solution comprised of 10 μL 60:40 acetonitrile ("ACN"):$H_2O$:0.1% TFA (v/v). For reverse-phase liquid chromatography, samples should start in aqueous solution, thus samples are vacuum-centrifuged until 1 μL of solution remained, and reconstituted in 5 μL $H_2O$ with 0.1% TFA (v/v). Samples (5 μL) are injected onto the column and separated using a gradient elution. Target compounds are quantified by summing the height of known fragment peaks in the LC-$MS^3$ spectra. The serum concentration and CSF concentration estimates are calculated using a calibration curve, accounting for the dilution factors and the probe recoveries for each experiment. Standards are matrix-matched to samples and underwent the same sample preparation steps.

The effect of glycosylation on three classes of peptide-based drugs are investigated, from fragmentation properties in the instrument during method development and quantitation, to their in vivo behavior. The efficacy of glycosylation of peptide-based drugs regarding their in vivo stability and BBB penetration are measured across different peptide modifications. This allows development of more biocompatible drugs with higher specificity and fewer side effects, while avoiding the inherent limitations of current peptide-based drugs.

Alternatively, older and less innovative injection and microdialysis methods of single drugs combined with $MS^2$ analysis can be used. This method is slower, but can also be used to measure the stability and BBB penetration of glycopeptides.

Example 4. Determination of the Analgesic Efficacy and Side Effect Profile

Cyclic oligopeptides of the invention are analyzed for their efficacy in managing acute and chronic pain, as well as their side effect profile. Tests have determined cyclic oligopeptides of the invention were efficacious in managing acute tail flick pain and chronic CIPN pain (see FIGS. 4A-4C). These pain types have shown to be translatable and relevant to patient populations with medical need. Side effect testing is also desirable to determine the clinical utility of cyclic oligopeptides of the invention as non-opioid analgesics. Cyclic oligopeptides of the invention are also tested for the "opioid-like" side effect of reward and abuse liability by conditioned place preference (CPP). The general dose-limiting side effects of dependence/withdrawal, tolerance with repeated dosing, and generalized motor dysfunction is tested by Rotarod testing. "OT-like" side effects is also tested by measuring anxiogenic or anxiolytic effects in the elevated plus maze. "AVP-like" side effects is also tested by measuring blood pressure changes using a tail cuff blood pressure monitoring system.

Testing of a Series of cyclic oligopeptides. Whether glycosylation can induce biousian behavior is determined as outlined below. Compounds 2LS118-1 through 2LS118-3 (see Table 1) experimented with different residues at amino acid positions 1 and 6 as well as different directions of the amide bond linkage. Compounds 2LS118-4 through 2LS118-6 maintained the $Asp_1 \rightarrow Dap^6$ amide linkage while adding varying glucosides at the C-terminus.

Figure 4A:
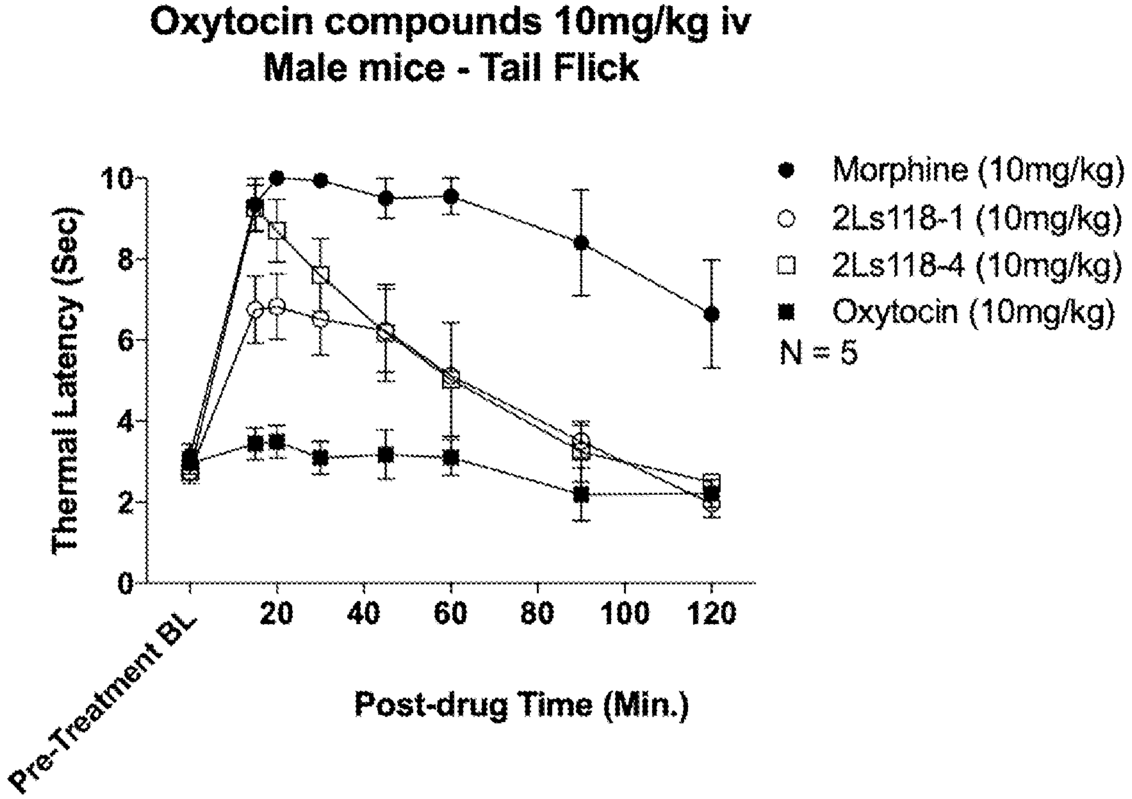
FIG. 4A is a graph showing results of 52° C. warm water tail flick assay (10 second cutoff) of male and female CD-1 mice injected iv with native oxytocin, compound 2LS118-1, compound 2LS118-4, or morphine all at 10 mg/kg. Vehicle: USP saline. Data are reported as mean±SEM, sample sizes of mice/group noted in the legends. Native OT produced no effect while compound 2LS118-1 and compound 2LS118-4 produced almost half to full maximal efficacy vs. morphine.
Figure 4B:
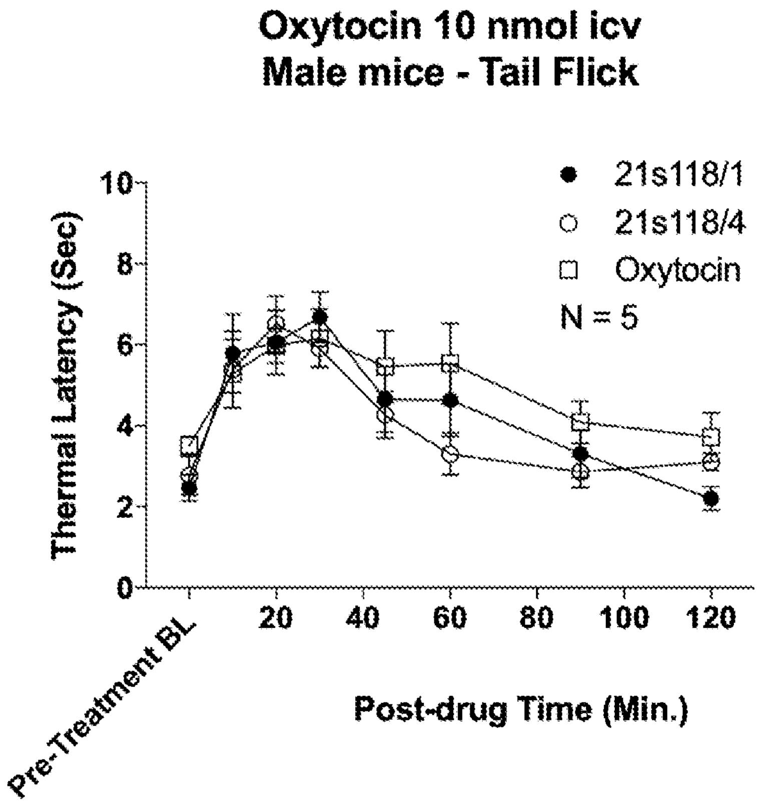
FIG. 4B is a graph showing results of 52° C. warm water tail flick assay (10 second cutoff) of male and female CD-1 mice injected icv with native OT, compound 2LS118-1, or compound 2LS118-4 all at 10 nmol. Vehicle: USP water. Each cyclic oligopeptide of the invention produced substantially equivalent anti-nociception ($p>0.05$).
Figure 4C:
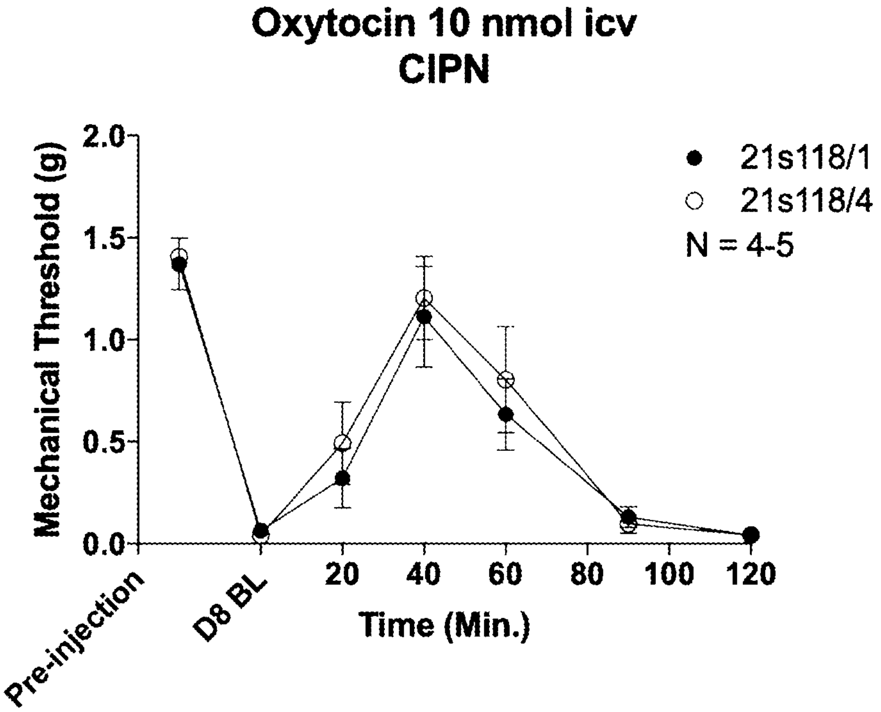
FIG. 4C is a graph showing results of Von Frey filaments test for mechanical threshold of male and female CD-1 mice injected icv with compound 2LS118-1 or compound 2LS118-4 at 10 nmol each. CIPN was induced by 2 mg/kg paclitaxel on days 1, 3, 5, 7. Compounds of the invention were injected icv at 10 nmol each on day 8. Both produced substantially equivalent anti-nociception in this chronic neuropathic pain model. Vehicle: USP water.

Cyclic oligopeptides 2LS118-1 ($Asp^1 \rightarrow Dap^6$ amide) and 2LS118-4 ($Asp^1 \rightarrow Dap^6$ amide with $SerGlc^9$) were tested along with the native OT peptide in antinociception models in mice. The compounds were administered by the intravenous (iv) route at 10 mg/kg while performing a 52° C. warm water tail flick assay. As expected, it was found that native OT peptide produced no anti-nociception (FIG. 4A). In contrast, 2LS118-1 produced approximately half-maximal efficacy, while 2LS118-4 produced near-maximal efficacy comparable to 10 mg/kg morphine by the same route (FIG. 4A). All 3 compounds were then injected by the intracerebroventricular (icv) route at a 10 nmol dose, and found that all 3 produced the same degree and duration of anti-nociceptive activity in the tail flick test (FIG. 4B). These results demonstrate that cyclic oligopeptides of the invention possess the same intrinsic anti-nociceptive activity as native OT when injected into the brain, but produce contrasting strong activity when injected peripherally. These results further show that cyclic oligopeptides of the invention have improved the druggability of native OT, either through enhancing metabolic stability, BBB penetration, or both. It was also found that cyclic oligopeptide 2LS118-4 produced a significantly higher peak effect than 2LS118-1. Without being bound by any theory, it is believed that this is due to an enhanced ability to penetrate the BBB by the presence of a glucoside residue. It was also found that both 2LS118-1 and 2LS118-4 produced high anti-nociceptive efficacy when injected icv (10 nmol) in a mouse model of chemotherapy-induced peripheral neuropathy (CIPN), demonstrating that cyclic oligopeptides of the invention are also efficacious in chronic neuropathic pain (FIG. 4C). These results indicate cyclic oligopeptides are efficacious with systemic injection in acute and chronic pain.

Tail Flick Assay: A tail flick assay (10 sec cutoff) is performed using naïve male and female CD-1 mice. Test compounds are delivered iv or sc with initial doses of around ≤10 mg/kg. It is expected that sc delivery could lengthen the duration of action due to the drug depot effect. Morphine (1, 3.2, 10 mg/kg) is used for comparison, as native OT has no efficacy when delivered peripherally (FIG. 4A). At least 3 different doses are used to create dose/response curves, which is used to calculate the potency ($A_{50}$).

CIPN is induced by 2 mg/kg ip injection of paclitaxel on days 1, 3, 5, and 7 with testing on day 8. Cyclic oligopeptides and morphine (as a positive control) are dosed and analyzed as for the tail flick assay, with mechanical allodynia measured using Von Frey filaments.

CPP induced by an $A_{50}$ dose of cyclic oligopeptides of the invention and 3.2 mg/kg sc morphine positive control is measured using a 3-chambered CPP box with male and female CD-1 mice. This assay was previously measured by the present inventors to measure morphine CPP. Four (4) daily conditioning trials are used, with injection of drug in the morning, a 15 minute period to reach peak drug effect, then confinement to the paired chamber for 10 minutes. Each afternoon the mice received a saline injection and are placed in the unpaired chamber for 10 minutes. On day 5 place preference are measured as the percent time spent in each chamber over a 10 minute period.

Potential dependence in male and female CD-1 mice is established by dosing with an $A_{90}$ dose of cyclic oligopeptides of the invention and 10 mg/kg morphine by the iv or sc route twice a day for 4 days. To test for involvement of the opioid system, withdrawal is precipitated with 30 mg/kg naloxone ip and withdrawal behaviors recorded for 20 minutes. To test for anxiogenic effects from cyclic oligopeptides of the invention withdrawal, the mice are injected with the OT antagonist L-368,899 (10 mg/kg, sc) and anxiety measured in the elevated plus maze as described below.

Tolerance: Male and female CD-1 mice are dosed with cyclic oligopeptides of the invention or morphine positive control (10 mg/kg) by the iv or sc route twice a day for 4 days. After each morning injection, tail flick anti-nociception are measured. The data are used to calculate time/response curves, which gives the rate of tolerance for each drug.

Rotarod: Male and female CD-1 mice received 3 training sessions on a Rotarod device (4-16 rpm). Cyclic oligopeptides of the invention at an $A_{90}$ dose or morphine positive control (10 mg/kg, iv or sc) are then injected with a 10 minute treatment time, then the mice are be tested on the Rotarod for 3 minutes. Latency to fall are recorded, with a low latency to fall associated with drug-induced motor dysfunction.

Elevated Plus Maze: Male and female CD-1 mice are injected with an $A_{90}$ dose of cyclic oligopeptides of the invention iv or sc or morphine (10 mg/kg, sc) or SNC80 (3.2 mg/kg, sc) positive controls. The mice are treated for 10 minutes, then placed in an elevated plus maze and their behavior recorded for 5 minutes. Time spent in the open arms is associated with anxiolysis, and in the closed arms with anxiogenesis.

Blood Pressure Measurement: Male and female CD-1 mice are injected with an $A_{90}$ dose of cyclic oligopeptides of the invention iv or sc or native AVP (10 mg/kg, iv) positive controls. The site of action of AVP on blood pressure is in the periphery, so the native peptide will be an acceptable control. Blood pressure are continually monitored 10 minutes before and 30 minutes after injection using a tail cuff blood pressure monitoring system. It is expected that cyclic oligopeptides of the invention will produce no blood pressure changes.

It is expected that cyclic oligopeptides of the invention will show strong efficacy and duration of action in tail flick and CIPN pain, based on data shown in FIGS. 4A-4C. Since cyclic oligopeptides of the invention have shown no reward liability, it is expected that no positive (or negative) CPP will be observed with cyclic oligopeptides of the invention. In addition no opioid-like withdrawal, no anxiogenic withdrawal, and no motor dysfunction are observed with cyclic oligopeptides of the invention. By maximizing OXTR selectivity vs. AVP receptors, it is expected AVP-like side effects including blood pressure changes are avoided.

Figures 5, 6:
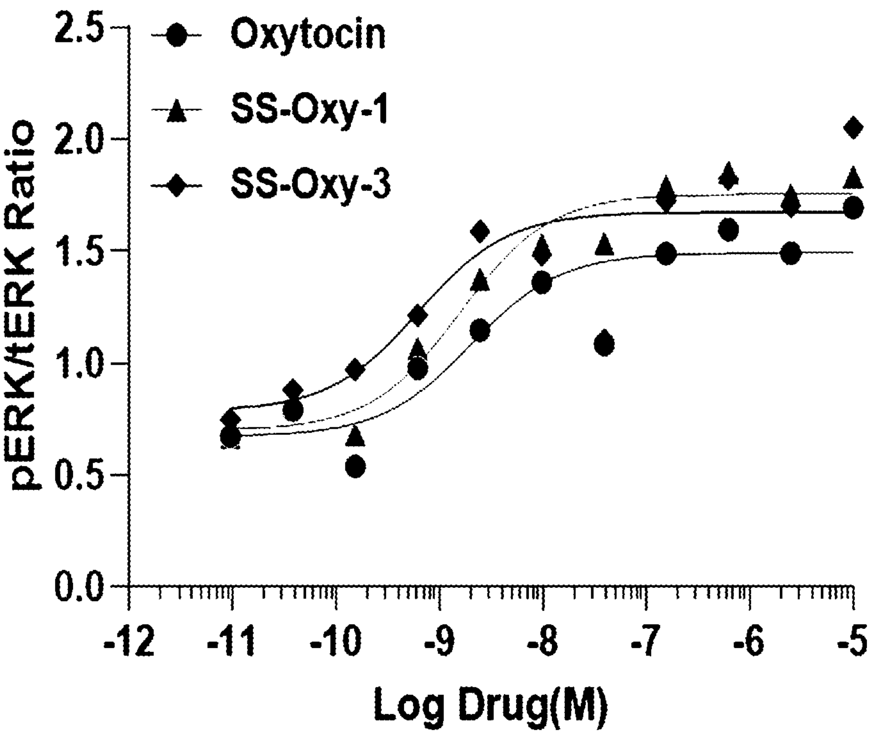
FIG. 5 is a graph showing activity of some of the cyclic oligopeptides of the invention compared to oxytocin on OXTR.
FIG. 6 is a table showing $EC_{50}$ for OXTR agonistic activity for some of the representative cyclic oligopeptides of the invention.
Figure 7A:
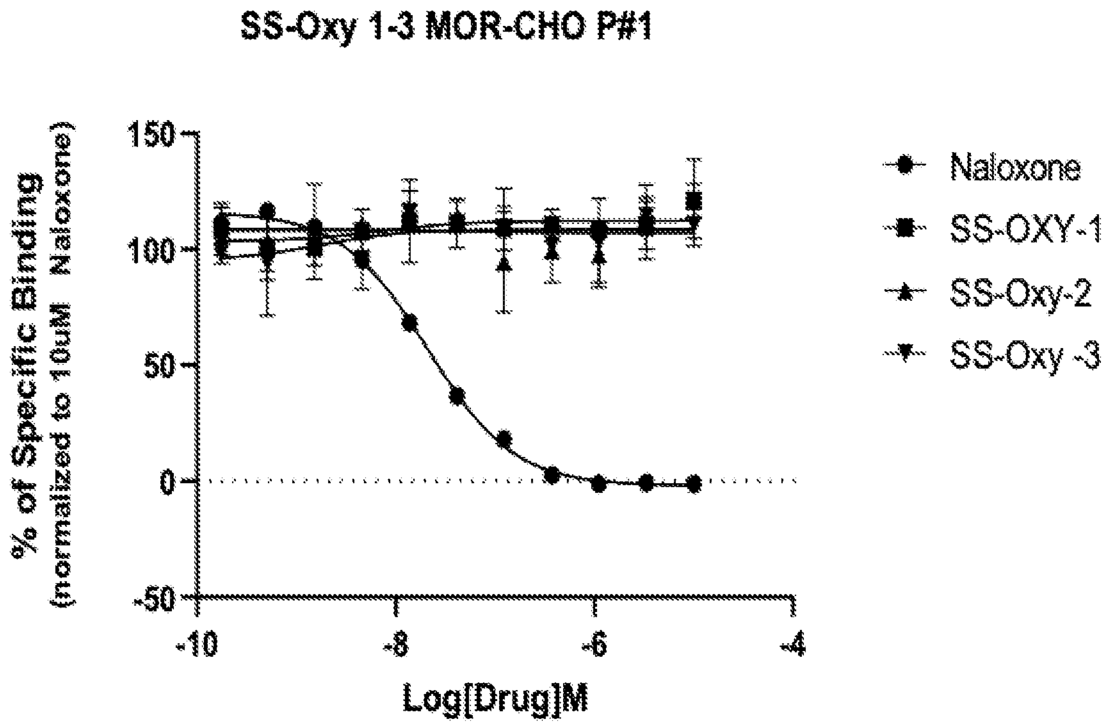
FIGS. 7A-7C are graphs showing results of experiments 1, 2, and 3, respectively, of binding to MOR by cyclic oligopeptides SSOXY1, SSOXY2, and SSOXY3 compared to naloxone.
Figure 7B:
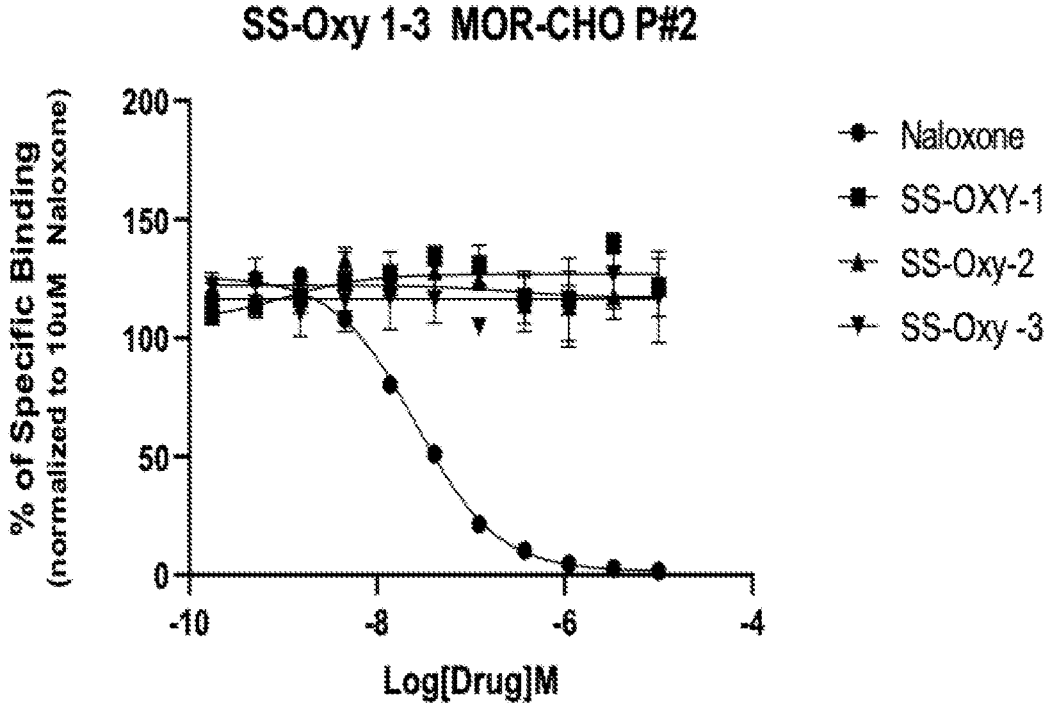
Figure 7C:
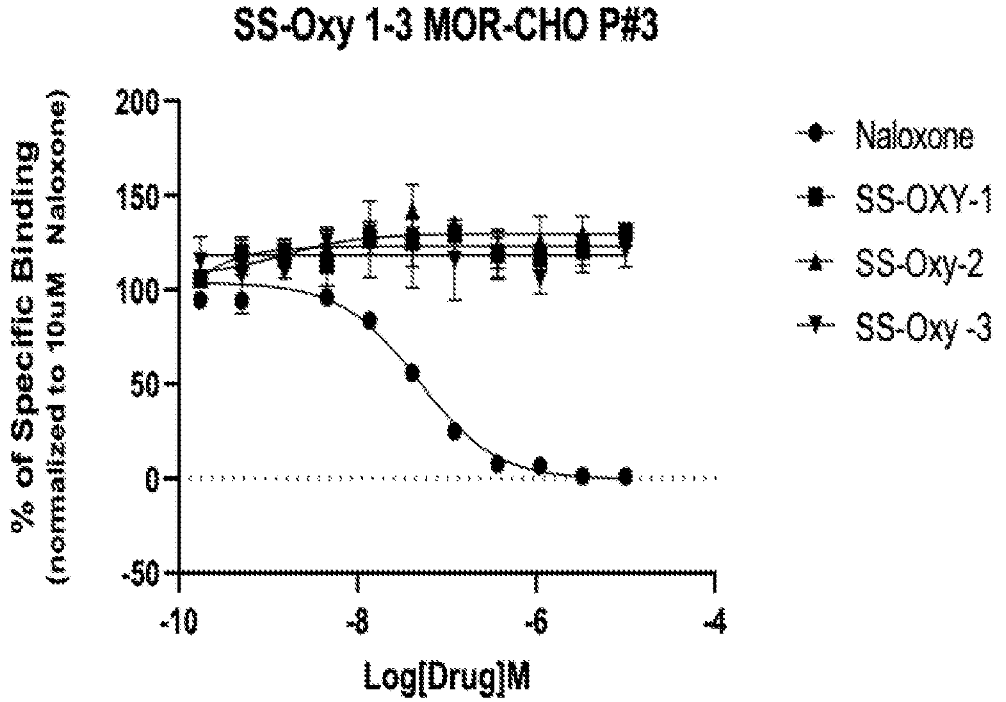
Figure 8A:
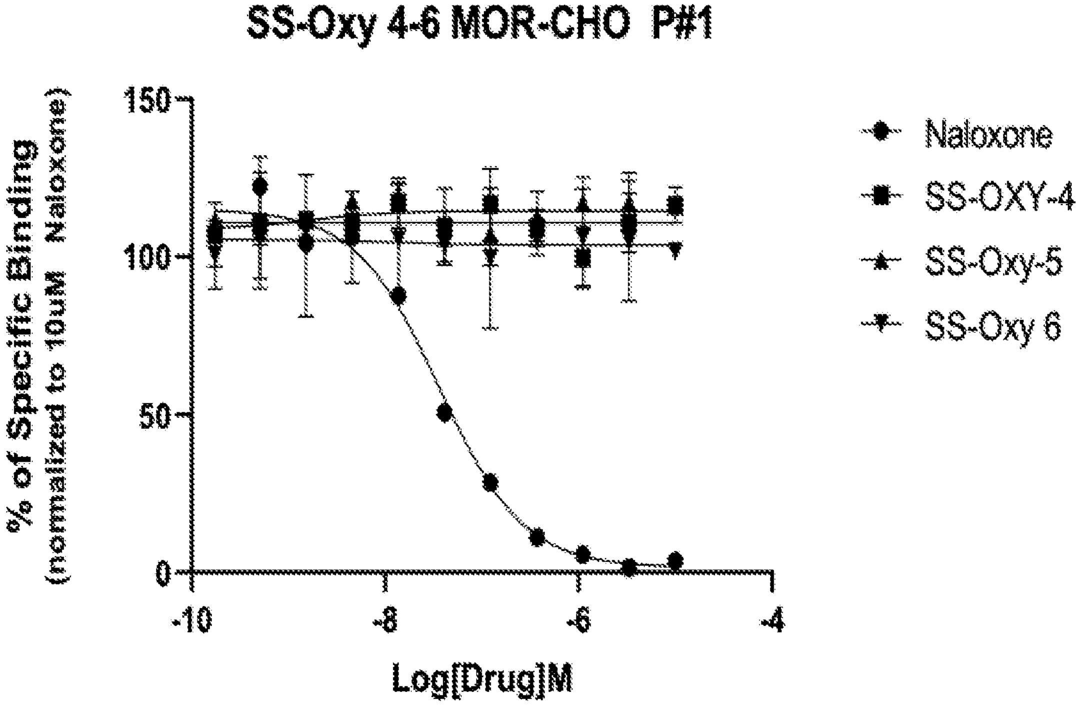
FIGS. 8A-8C are graphs showing results of experiments 1, 2, and 3, respectively, of binding to MOR by cyclic oligopeptides SSOXY4, SSOXY5, and SSOXY6 compared to naloxone.
Figure 8B:
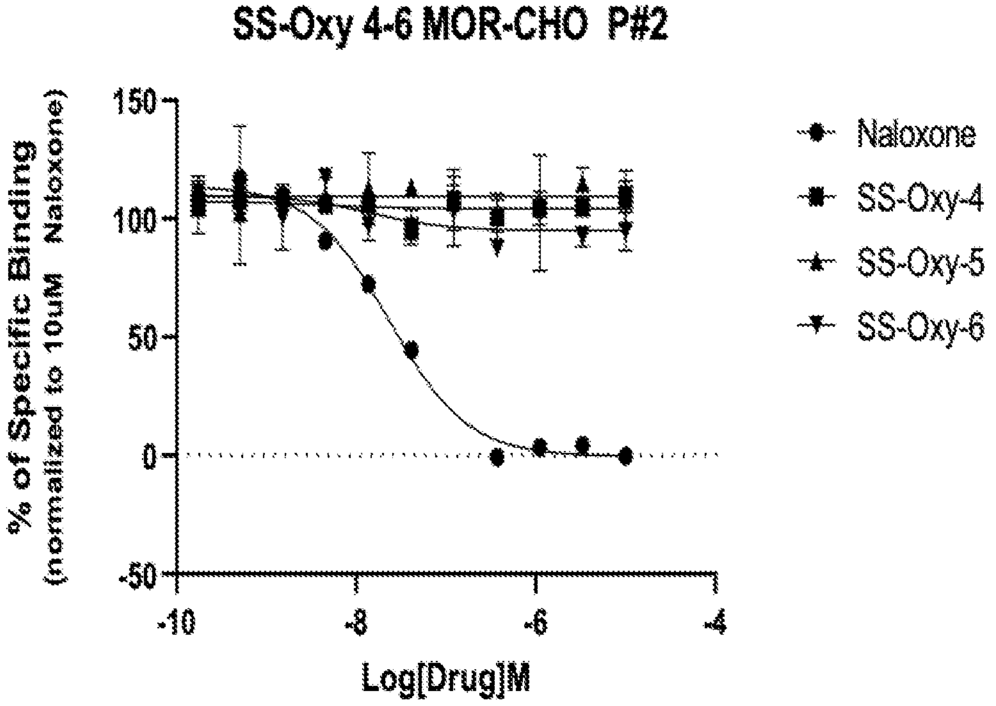
Figure 8C:
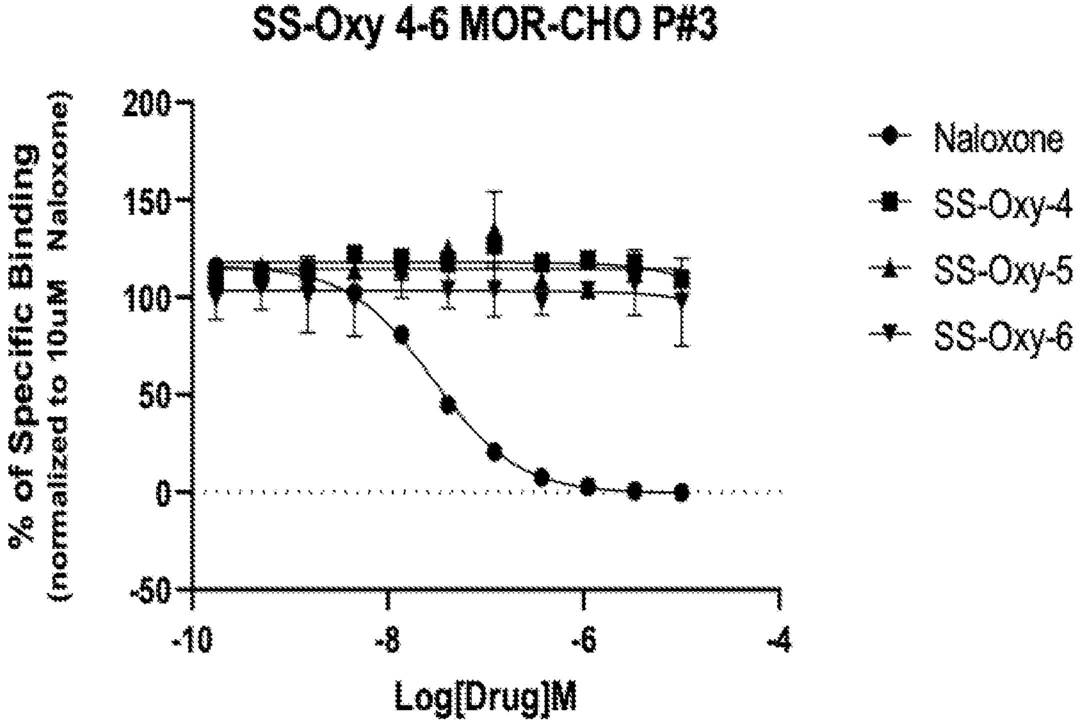
Figure 9A:
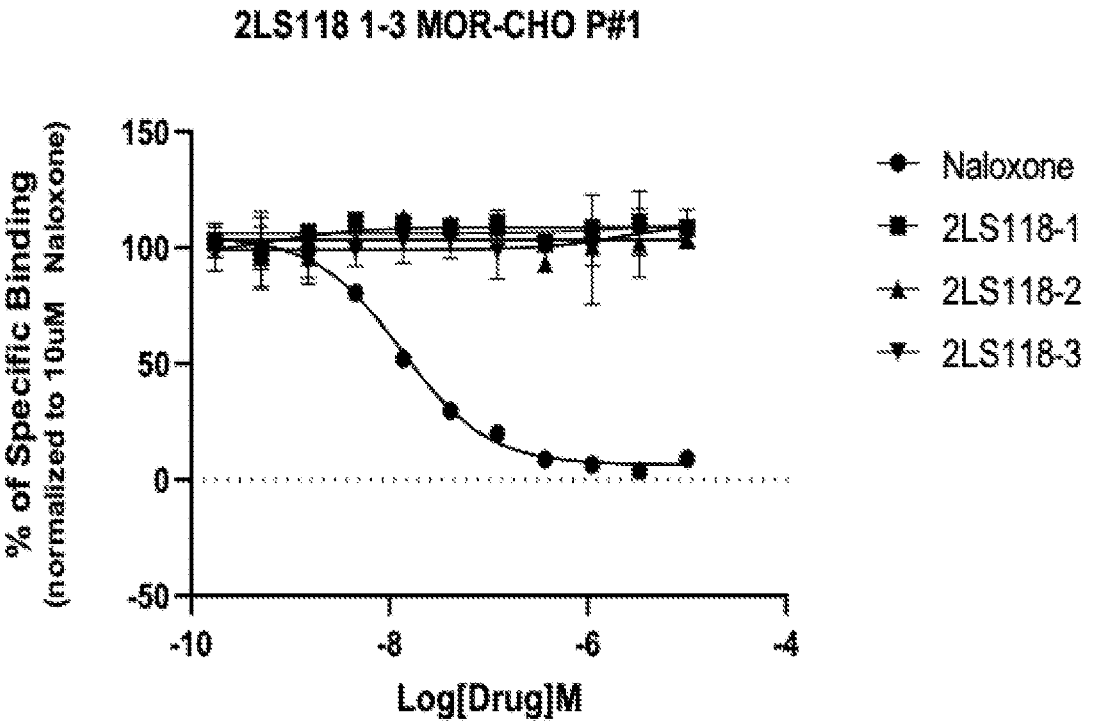
FIGS. 9A-9C are graphs showing results of experiments 1, 2, and 3, respectively, of binding to MOR by cyclic oligopeptides 2LS118-1, 2LS118-2, and 2LS118-3 compared to naloxone.
Figure 9B:
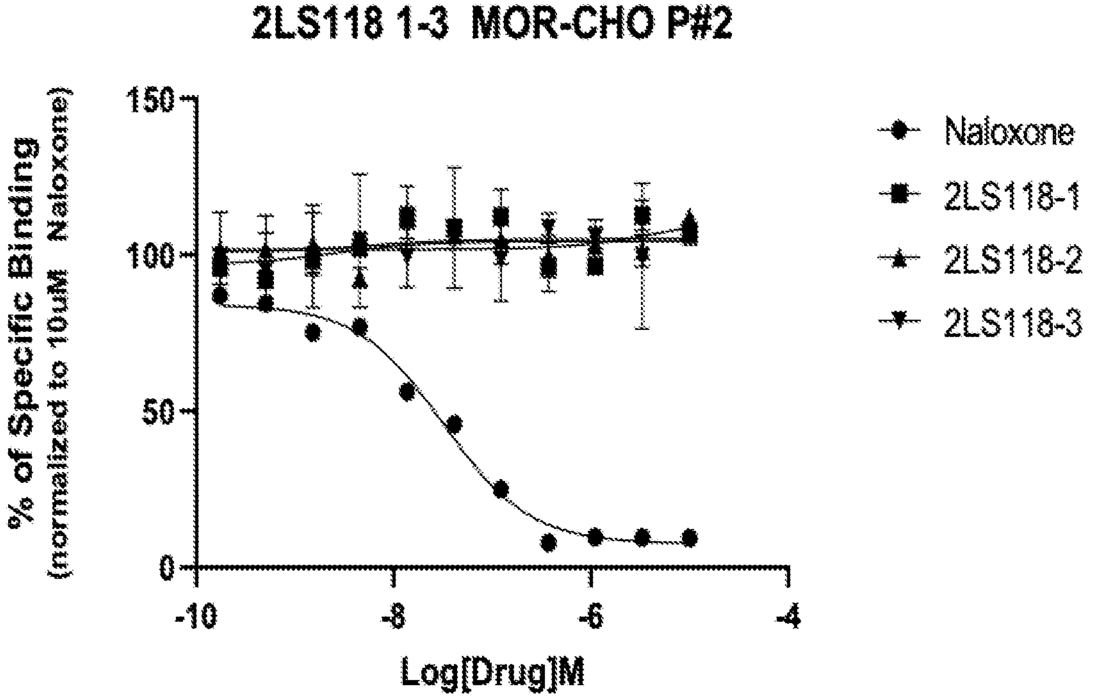
Figure 9C:
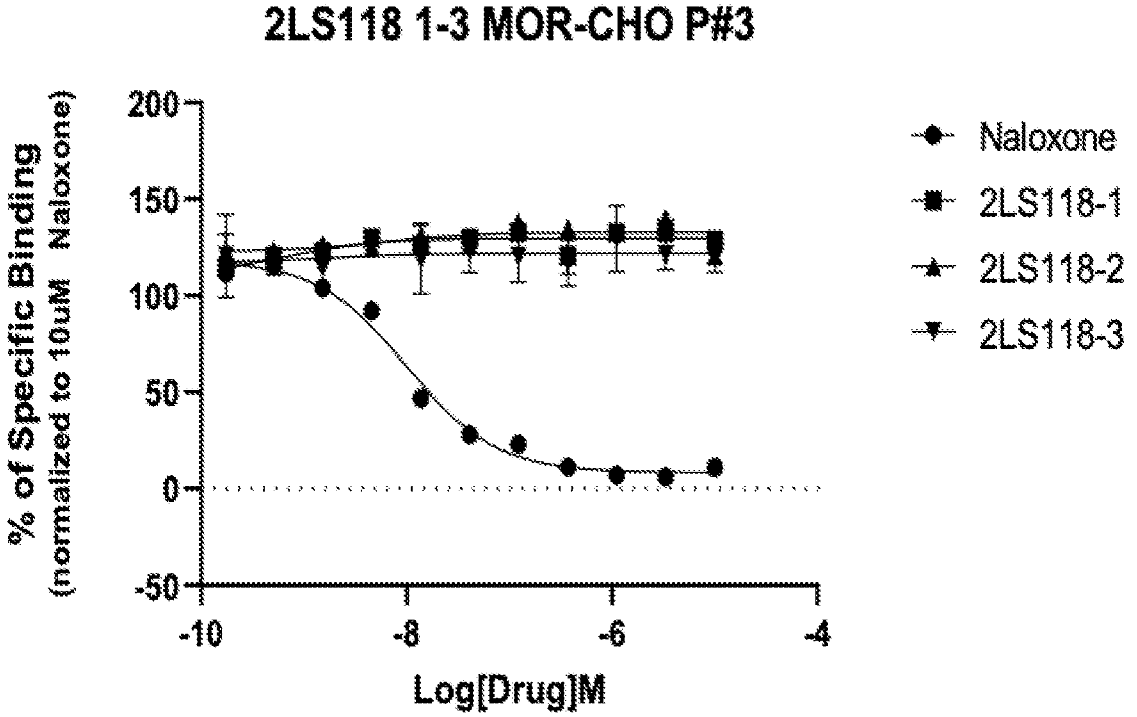
Figure 10A:
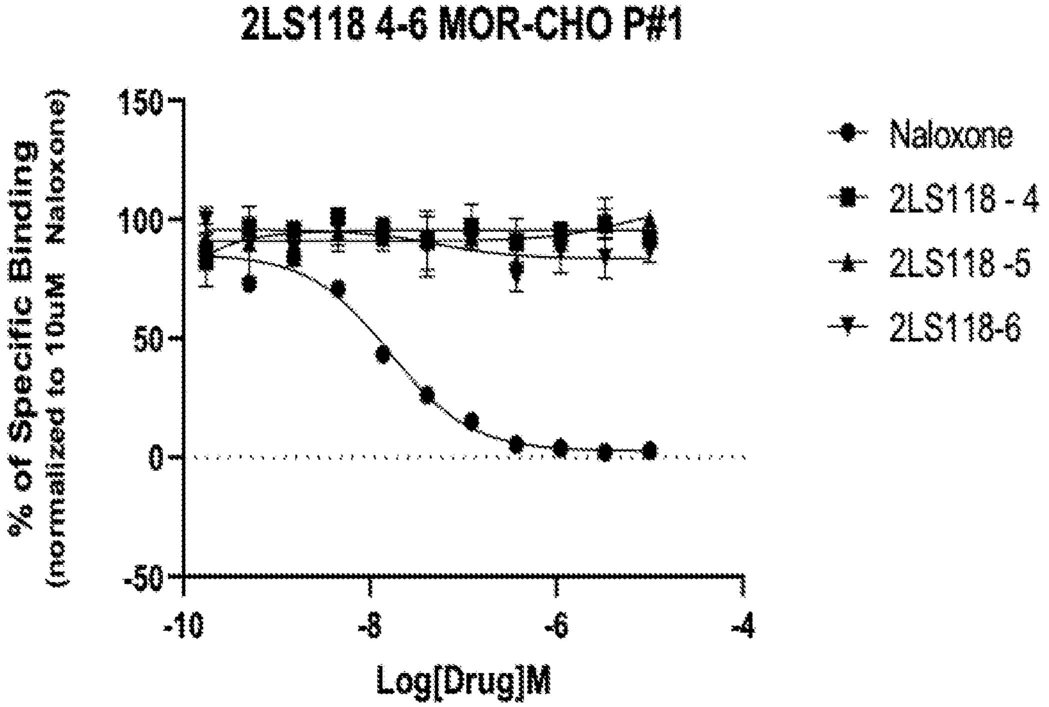
FIGS. 10A-10C are graphs showing results of experiments 1, 2, and 3, respectively, of binding to MOR by cyclic oligopeptides 2LS118-4, 2LS118-5, and 2LS118-6 compared to naloxone.
Figure 10B:
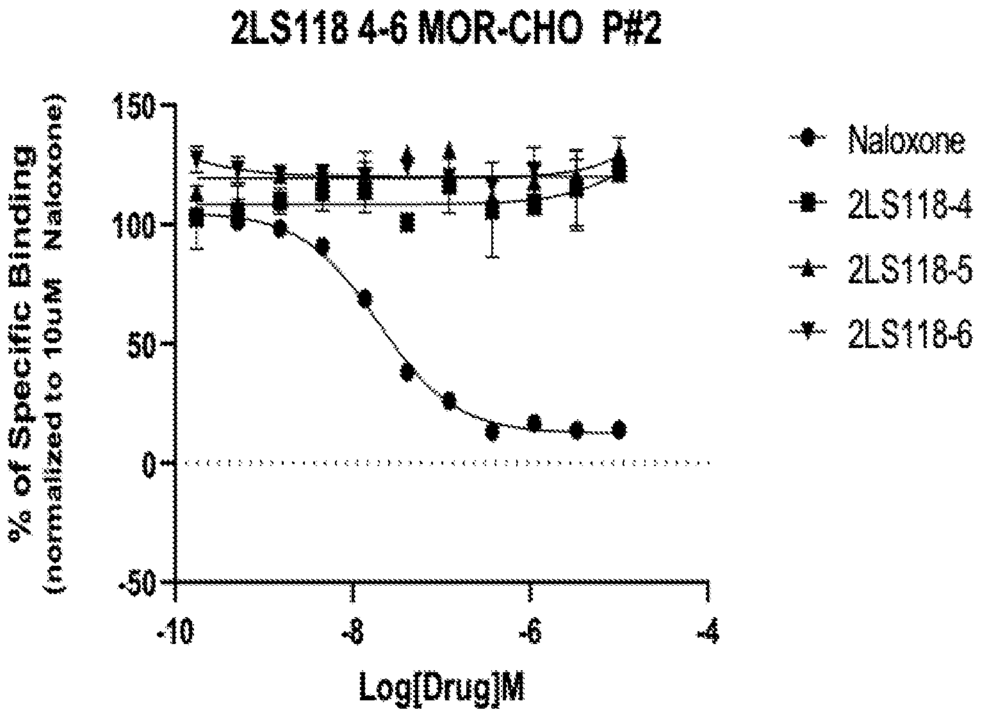
Figure 10C:
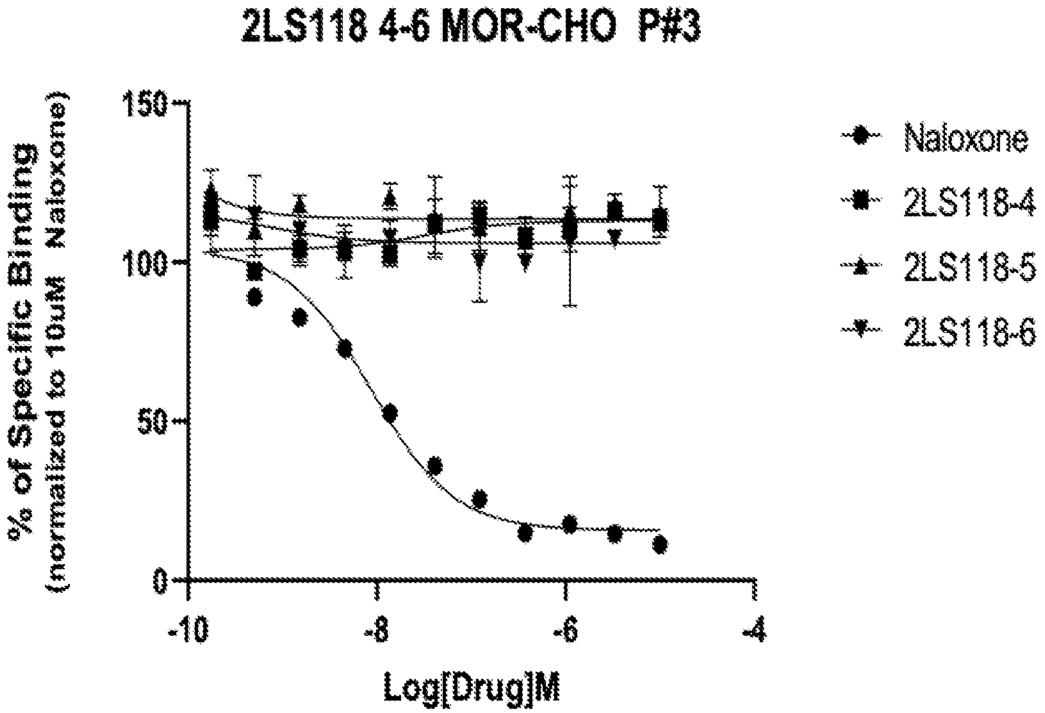

Example 5: Activity of Cyclic Oligopeptides of the Invention on OXTR and Mu Opioid Receptor Activity of cyclic oligopeptides of the invention on OXTR: Cell culture assays were conducted to evaluate the pharmacodynamics of representative samples of cyclic glycopeptides of the invention. First, ERK MAPK activation was evaluated using an In Cell Western assay using human OXTR-expressing CHO cells. In FIG. 5, phosophorylated ERK was normalized to total ERK (pERK/tERK ratio) and used to calculate compound potency of agonist activation at the receptor. Representative curves along with summary numerical values are shown for each compound, showing that a number of representative cyclic glycopeptides of the invention retain highly potent OXTR agonist activity. $EC_{50}$ for OXTR agonistic activity for some of the representative cyclic oligopeptides of the invention are shown in FIG. 6.

Competition Binding at MOR-CHO(PE) Presence of [3H] Diprenorphine: The compounds were also tested for off-target binding to the human Mu Opioid Receptor (MOR), also expressed in CHO cells. Briefly, the experiment involved: Protein: MOR-CHO(PE) Passage: 16; previously frozen cell pellets used and prepared. Protein 15 ug/well used. Serial dilution of compounds and Naloxone (control) used. Total binding absence of compound used, 10 uM Naloxone used for nonspecific binding. Each well contained membrane 15 ug/well protein and 2.48 nM Radioligand final conc. Incubated 1 hour in R/T; harvested on GF/B filter, dried O/N. Data are normalized to % Specific binding. MOR-CHO(PE) cell Kd: 5.27±2.39 nM. Data are expressed as mean of a single experiment, performed in triplicate. Vehicle contained 0.1% DMSO and 0.1% BSA. (Radioligand: #23067 Lot: 2548344 NET: 1121250UC). Results of binding assay at MOR-CHO are shown in FIG. 7A-10C. Table 1 below also summarizes overall MOR binding profile of cyclic oligopeptides of the invention compared to naloxone.

TABLE 1

MOR Profile of Naloxone and cyclic oligopeptides

| | IC50(nM) | Ki(nM) |
|---|---|---|
| Naloxone | 13 | 9 |
| 2LS 118-1 | >2500 | >2500 |
| 2LS118-2 | >2500 | >2500 |
| 2LS118-3 | >2500 | >2500 |
| 2LS118-4 | >2500 | >2500 |
| 2LS118-5 | >2500 | >2500 |
| 2LS118-6 | >2500 | >2500 |
| SS-Oxy 1 | >2500 | >2500 |
| SS-Oxy 2 | >2500 | >2500 |
| SS-Oxy 3 | >2500 | >2500 |
| SS-Oxy 4 | >2500 | >2500 |
| SS-Oxy 5 | >2500 | >2500 |
| SS-Oxy 6 | >2500 | >2500 |

As the results clearly show, there was no significant binding to mu opioid receptor (MOR) by of any of the tested cyclic glycopeptides of the invention. These results indicate analgesic activity of cyclic oligopeptides of the invention is due to OXTR activation and not off-target MOR activation. Because there is no significant activity on MOR, it is expected that no addictive side-effects shown in opioid based pain medications, such as morphine, will be present in cyclic oligopeptides of the invention.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A cyclic oligopeptide of the formula:

I (SEQ ID NO:3)

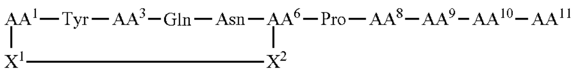

or a pharmaceutically acceptable salt thereof, or a solvate thereof, wherein one of $AA^1$ or $AA^6$ is an amino acid having a carboxylate side-chain functional group and the other is an amino acid having an amine side-chain functional group such that $X^1$ and $X^2$ together form an amide bond;

$AA^3$ is Phe or Ile;

$AA^9$ is Arg, Leu, or Aib;

both of $AA^9$ and $AA^{10}$ are absent; and $AA^{11}$ is Ser, or Thr, and wherein at least one amino acid residues in said cyclic oligopeptide is glycosylated.

2. The cyclic oligopeptide of claim 1, wherein one of $AA^1$ and $AA^6$ is aspartic acid or glutamic acid and the other is lysine, ornithine, diaminobutyric acid (DABA), or 2,3-diaminopropionic acid (DAPA).

3. The cyclic oligopeptide of claim 1, wherein said amino acid is glycosylated with a monosaccharide or a disaccharide.

4. The cyclic oligopeptide of claim 3, wherein said monosaccharide comprises allose, altrose, glucose, mannose, gulose, idose, galactose, talose, ribose, arabinose, xylose, lyxose, psicose, sorbose, tagatose, ribulose, or xylulose.

5. The cyclic oligopeptide of claim 3, wherein said disaccharide comprises sucrose, lactose, maltose, gentabiose cellobiose, lactulose, chitobiose, fructose, sorbose, tagatose, ribulose, or xylulose.

6. The cyclic oligopeptide of claim 3, wherein said monosaccharide is an (L)-isomer.

7. The cyclic oligopeptide of claim 3, wherein said monosaccharide is a (D)-isomer.

8. The cyclic oligopeptide of claim 3, wherein at least one monosaccharide unit of said disaccharide is an (L)-isomer.

9. The cyclic oligopeptide of claim 1, wherein $AA^{11}$ is glycosylated serine or threonine.

10. The cyclic oligopeptide of claim 1, wherein one of $AA^1$ or $AA^6$ is an amino acid having a carboxylate side-chain and the other is 2,3-diaminopropionic acid or 2,4-diaminobutyric acid.

11. The cyclic oligopeptide of claim 10, wherein said amino acid having a carboxylate side-chain is aspartic acid or glutamic acid.

12. The cyclic oligopeptide of claim 1, wherein $AA^8$ is Leu or Aib.

13. A method for treating a clinical condition to a subject in need of such a treatment, said method comprising administering to said subject a therapeutically effective amount of a cyclic oligopeptide of the formula:

I (SEQ ID NO:3)

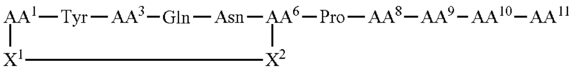

or a pharmaceutically acceptable salt thereof, a solvate thereof, or a combination thereof, wherein one of $AA^1$ or $AA^6$ is an amino acid having a carboxylate side-chain functional group and the other is an amino acid having an amine side-chain functional group such that $X^1$ and $X^2$ together form an amide bond;

$AA^3$ is Phe or Ile;

$AA^9$ is Arg, Leu, or Aib;

both of $AA^9$ and $AA^{10}$ are absent; and $AA^{11}$ is Ser, or threonine, wherein at least one amino acid residues in said cyclic oligopeptide is glycosylated, and wherein said clinical condition is selected from the group consisting of chronic pain, acute pain, opioid addiction, alcohol addiction, or other addictive behaviors, Autism Spectrum Disorders, Asperger's Syndrome, and a combination thereof.

14. The method of claim 13, wherein $AA^{11}$ is glycosylated.

15. The method of claim 14, wherein said $AA^{11}$ is serine.

* * * * *

SEQUENCE LISTING

```
<160> NUMBER OF SEQ ID NOS: 16

<210> SEQ ID NO 1
<211> LENGTH: 9
<212> TYPE: PRT
<213> ORGANISM: Homo sapiens
<220> FEATURE:
<221> NAME/KEY: DISULFID
<222> LOCATION: (1)..(6)
<223> OTHER INFORMATION: Forms cyclic structure via disulfide linkage

<400> SEQUENCE: 1

Cys Tyr Ile Gln Asn Cys Pro Leu Gly
1               5


<210> SEQ ID NO 2
<211> LENGTH: 11
<212> TYPE: PRT
```

```
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (1)..(1)
<223> OTHER INFORMATION: one of amino acid on 1-position and 6-position
      is an amino acid having a carboxylate side-chain functional group
      and the other is an amino acid having an amine side-chain
      functional group such that X1 and X2 together form an amide bond
<220> FEATURE:
<221> NAME/KEY: CARBOHYD
<222> LOCATION: (1)..(11)
<223> OTHER INFORMATION: optionally at least one amino acid residues is
      glycosylated
<220> FEATURE:
<221> NAME/KEY: MISC_FEATURE
<222> LOCATION: (2)..(5)
<223> OTHER INFORMATION: each is independently natural or unnatural
      amino acid
<220> FEATURE:
<221> NAME/KEY: MISC_FEATURE
<222> LOCATION: (6)..(6)
<223> OTHER INFORMATION: one of amino acid on 1-position and 6-position
      is an amino acid having a carboxylate side-chain functional group
      and the other is an amino acid having an amine side-chain
      functional group such that X1 and X2 together form an amide bond
<220> FEATURE:
<221> NAME/KEY: MISC_FEATURE
<222> LOCATION: (7)..(11)
<223> OTHER INFORMATION: each is independently natural or unnatural
      amino acid
<220> FEATURE:
<221> NAME/KEY: MISC_FEATURE
<222> LOCATION: (9)..(10)
<223> OTHER INFORMATION: each can indpendently be absent

<400> SEQUENCE: 2

Xaa Xaa Xaa Xaa Xaa Xaa Xaa Xaa Xaa Xaa Xaa
1               5                   10


<210> SEQ ID NO 3
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (1)..(1)
<223> OTHER INFORMATION: one of amino acid on 1-position and 6-position
      is an amino acid having a carboxylate side-chain and the other is
      a carboxylic acid having an amine functional group on the side-
      chain such that X1 and X2 together form an amide bond
<220> FEATURE:
<221> NAME/KEY: MISC_FEATURE
<222> LOCATION: (3)..(3)
<223> OTHER INFORMATION: any natural or unnatural amino acid, preferably
      Phe or Ile
<220> FEATURE:
<221> NAME/KEY: MISC_FEATURE
<222> LOCATION: (6)..(6)
<223> OTHER INFORMATION: one of amino acid on 1-position and 6-position
      is an amino acid having a carboxylate side-chain and the other is
      a carboxylic acid having an amine functional group on the side-
      chain such that X1 and X2 together form an amide bond
<220> FEATURE:
<221> NAME/KEY: MISC_FEATURE
<222> LOCATION: (8)..(8)
```

```
<223> OTHER INFORMATION: any natural or unnatural amino acid, preferably
      Arg, Leu, or Aib
<220> FEATURE:
<221> NAME/KEY: MISC_FEATURE
<222> LOCATION: (9)..(10)
<223> OTHER INFORMATION: any natural or unnatural amino acid, preferably
      is independently Gly, Ser, Cys, Thr or an analog thereof, or
      absent
<220> FEATURE:
<221> NAME/KEY: MISC_FEATURE
<222> LOCATION: (11)..(11)
<223> OTHER INFORMATION: any natural or unnatural amino acid, preferably
      Gly, Ser, Cys, Thr or an analog thereof

<400> SEQUENCE: 3

Xaa Tyr Xaa Gln Asn Xaa Pro Xaa Xaa Xaa Xaa
1               5                   10


<210> SEQ ID NO 4
<211> LENGTH: 9
<212> TYPE: PRT
<213> ORGANISM: Homo sapiens
<220> FEATURE:
<221> NAME/KEY: DISULFID
<222> LOCATION: (1)..(6)
<223> OTHER INFORMATION: Forms cyclic structure via a disulfide linkage

<400> SEQUENCE: 4

Cys Tyr Phe Gln Asn Cys Pro Arg Gly
1               5


<210> SEQ ID NO 5
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid

<400> SEQUENCE: 5

Asp Tyr Ile Gln Asn Xaa Pro Leu Gly
1               5


<210> SEQ ID NO 6
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid

<400> SEQUENCE: 6

Glu Tyr Ile Gln Asn Xaa Pro Leu Gly
1               5


<210> SEQ ID NO 7
<211> LENGTH: 9
```

<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (1)..(1)
<223> OTHER INFORMATION: 2,3-diaminopropionic acid

<400> SEQUENCE: 7

Xaa Tyr Ile Gln Asn Asp Pro Leu Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid
<220> FEATURE:
<221> NAME/KEY: CARBOHYD
<222> LOCATION: (9)..(9)
<223> OTHER INFORMATION: covalently linked to glucose

<400> SEQUENCE: 8

Asp Tyr Ile Gln Asn Xaa Pro Leu Ser
1               5

<210> SEQ ID NO 9
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid
<220> FEATURE:
<221> NAME/KEY: CARBOHYD
<222> LOCATION: (10)..(10)
<223> OTHER INFORMATION: covalently linked to glucose

<400> SEQUENCE: 9

Asp Tyr Ile Gln Asn Xaa Pro Leu Gly Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid
<220> FEATURE:
<221> NAME/KEY: CARBOHYD
<222> LOCATION: (10)..(11)
<223> OTHER INFORMATION: each covalently linked to glucose

<400> SEQUENCE: 10

Asp Tyr Ile Gln Asn Xaa Pro Leu Gly Ser Ser
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid
<220> FEATURE:
<221> NAME/KEY: CARBOHYD
<222> LOCATION: (9)..(9)
<223> OTHER INFORMATION: covalently linked to lactose

<400> SEQUENCE: 11

Asp Tyr Ile Gln Asn Xaa Pro Leu Ser
1               5

<210> SEQ ID NO 12
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid
<220> FEATURE:
<221> NAME/KEY: CARBOHYD
<222> LOCATION: (10)..(10)
<223> OTHER INFORMATION: covalently linked to lactose

<400> SEQUENCE: 12

Asp Tyr Ile Gln Asn Xaa Pro Leu Gly Ser
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid -continued
<220> FEATURE:
<221> NAME/KEY: MISC_FEATURE
<222> LOCATION: (8)..(8)
<223> OTHER INFORMATION: 2-Aminoisobutyric acid
<220> FEATURE:
<221> NAME/KEY: CARBOHYD
<222> LOCATION: (9)..(9)
<223> OTHER INFORMATION: covalently linked to glucose

<400> SEQUENCE: 13

Asp Tyr Ile Gln Asn Xaa Pro Xaa Ser
1 5

<210> SEQ ID NO 14
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid
<220> FEATURE:
<221> NAME/KEY: CARBOHYD
<222> LOCATION: (9)..(9)
<223> OTHER INFORMATION: covalently linked to glucose

<400> SEQUENCE: 14

Glu Tyr Ile Gln Asn Xaa Pro Leu Ser
1 5

<210> SEQ ID NO 15
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage
<220> FEATURE:
<221> NAME/KEY: MISC_FEATURE
<222> LOCATION: (6)..(6)
<223> OTHER INFORMATION: 2,3-diaminopropionic acid
<220> FEATURE:
<221> NAME/KEY: MISC_FEATURE
<222> LOCATION: (8)..(8)
<223> OTHER INFORMATION: 2-Aminoisobutyric acid
<220> FEATURE:
<221> NAME/KEY: CARBOHYD
<222> LOCATION: (9)..(9)
<223> OTHER INFORMATION: covalently linked to glucose

<400> SEQUENCE: 15

Glu Tyr Ile Gln Asn Xaa Pro Xaa Ser
1 5

<210> SEQ ID NO 16
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(6)
<223> OTHER INFORMATION: Forms cyclic structure via an amide linkage -continued

```
<220> FEATURE:
<221> NAME/KEY: MISC_FEATURE
<222> LOCATION: (6)..(6)
<223> OTHER INFORMATION: 2,3-diaminopropionic acid
<220> FEATURE:
<221> NAME/KEY: MISC_FEATURE
<222> LOCATION: (8)..(8)
<223> OTHER INFORMATION: 2-Aminoisobutyric acid
<220> FEATURE:
<221> NAME/KEY: CARBOHYD
<222> LOCATION: (10)..(10)
<223> OTHER INFORMATION: covalently linked to glucose

<400> SEQUENCE: 16

Glu Tyr Ile Gln Asn Xaa Pro Xaa Gly Ser
1               5                   10
```